(12) United States Patent
Toner et al.

(10) Patent No.: US 11,013,404 B2
(45) Date of Patent: May 25, 2021

(54) ADAPTIVE CONFIGURATION OF AN OPHTHALMIC DEVICE

(71) Applicant: Johnson & Johnson Vision Care, Inc., Jacksonville, FL (US)

(72) Inventors: Adam Toner, Jacksonville, FL (US); Donald K. Whitney, Melbourne, FL (US); Scott Humphreys, Greensboro, NC (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 421 days.

(21) Appl. No.: 16/143,308

(22) Filed: Sep. 26, 2018

(65) Prior Publication Data
US 2020/0093366 A1 Mar. 26, 2020

(51) Int. Cl.
| | |
|---|---|
| *A61B 3/113* | (2006.01) |
| *A61F 2/16* | (2006.01) |
| *A61B 5/11* | (2006.01) |
| *G02C 7/04* | (2006.01) |

(52) U.S. Cl.
CPC ............ *A61B 3/113* (2013.01); *A61B 5/1103* (2013.01); *A61F 2/1624* (2013.01); *G02C 7/041* (2013.01)

(58) Field of Classification Search
USPC ........................................................ 351/209
See application file for complete search history.

(56) References Cited

U.S. PATENT DOCUMENTS

2015/0087249 A1\* 3/2015 Pugh .................. G02C 7/04
455/90.3

\* cited by examiner

*Primary Examiner* — James C. Jones

(57) ABSTRACT

Methods and systems for adaptive configuration of ophthalmic devices are disclosed. An example method may comprise receiving, by a first sensor system disposed on or in a first ophthalmic device, sensor data representing movement of an eye of a user, wherein the first ophthalmic device is disposed within or upon an eye of the user; causing, based on the sensor data, storage of a history of movement of the eye; determining, based on the history of movement, a dwell characteristic indicating a distance at which the eye is fixated when an event occurs; and causing output of a signal indicative of performing an action in response to determining the dwell characteristic.

60 Claims, 16 Drawing Sheets

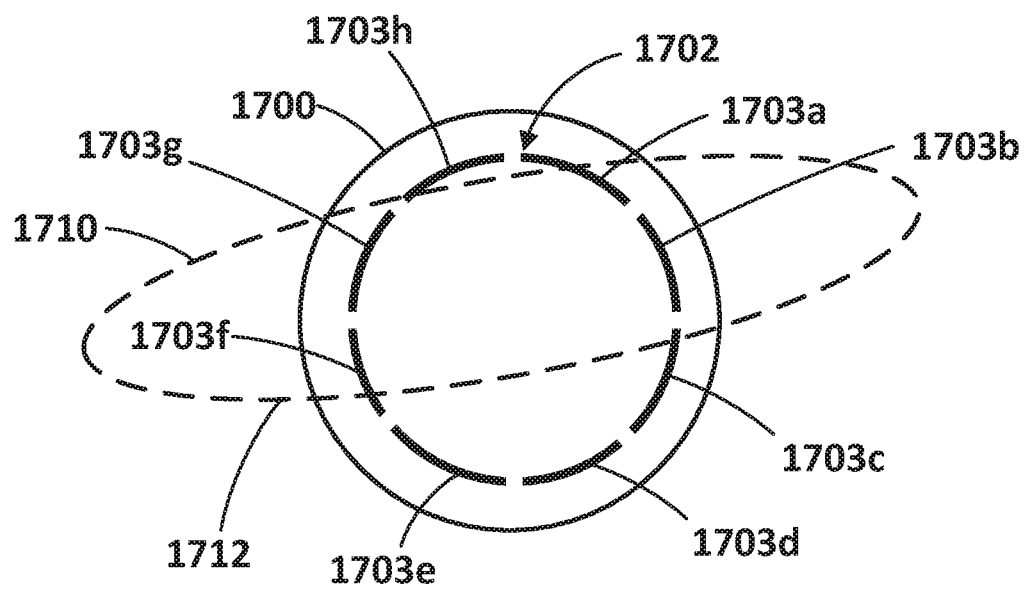

ADAPTIVE CONFIGURATION OF AN OPHTHALMIC DEVICE

TECHNICAL FIELD

The present disclosure relates to ophthalmic devices having embedded controlling elements, and more specifically, to the embedded controlling elements and method for using the same to adaptively adjust thresholds and other configuration settings of the ophthalmic devices.

BACKGROUND

Near and far vision needs exist for all. In young non-presbyopic patients, the normal human crystalline lens has the ability to accommodate both near and far vision needs and those viewing items are in focus. As one ages, the vision is compromised due to a decreasing ability to accommodate as one ages. This is called presbyopia.

Adaptive optics/powered lens products are positioned to address this and restore the ability to see items in focus. But, what is required is knowing when to "activate/actuate" the optical power change. While a manual indication or use of a key fob to signal when a power change is required is one way to accomplish this change. However, leveraging anatomical/biological conditions/signals may be more responsive, more user friendly and potentially more "natural" and thus more pleasant.

A number of things happen when we change our gaze from far to near. Our pupil size changes, our line of sight from each eye converge in the nasal direction coupled with a somewhat downward component as well. However, to sense/measure these items is difficult, one also needs to filter out certain other conditions or noise, (e.g., blinking, what to do when one is lying down, or head movements).

In reference to FIG. 4, when observing an object in each eye the visual axis points toward the object or Target. Since the two eyes are spaced apart (distance b) and the focal point is in front, a triangle is formed. Forming a triangle allows the relationship of angles ($\theta L$ and $\theta R$) of each visual axis to the distance (Y) the object is from the eyes to be determined. Since the distance (Y) is what determines if a change in optical power is required, then knowing the angles and the distance between the eyes and using simple math would allow a system to make a decision regarding when to change the optical power.

Sensing of multiple items may be required to remove/mitigate any false positive conditions that would indicate a power change is required when that is not the case. Use of an algorithm may be helpful. Additionally, threshold levels may vary from patient to patient, thus some form of calibration will likely be required as well.

An ophthalmic device may be configured to activate and/or perform various operations based on the presence of a characteristic. The thresholds for performing these operations may vary from user to user, and from situation to situation. Additionally, user behavior may not perfectly match the instructions provided by user. Thus, there is a need for more sophisticated ophthalmic devices that automatically determine user characteristics based on history of sensor data.

SUMMARY

A system of the present disclosure comprises a first ophthalmic device configured to be disposed within or upon an eye of a user and a first sensor system disposed in or on the first ophthalmic device. The first sensor system comprising a first sensor and a first processor operably connected to the first sensor and configured for: causing storage of a history of movement of the eye; determining, based on the history of movement, a dwell characteristic indicating a distance at which the eye is fixated when an event occurs; and causing output of a signal indicative of performing an action in response to determining the dwell characteristic.

According to another aspect of the present disclosure, a method comprising receiving, by a first sensor system disposed on or in a first ophthalmic device, sensor data representing movement of an eye of a user, wherein the first ophthalmic device is disposed within or upon an eye of the user; causing, based on the sensor data, storage of a history of movement of the eye; determining, based on the history of movement, a dwell characteristic indicating a distance at which the eye is fixated when an event occurs; and causing output of a signal indicative of performing an action in response to determining the dwell characteristic.

According to another aspect of the present disclosure, a system comprising a first ophthalmic device configured to be disposed within or upon an eye of a user, and a first sensor system disposed in or on the first ophthalmic device. The first sensor system comprising a first sensor and a first processor operably connected to the first sensor and configured for: causing storage of a history of movement of at least one of the eye or an eye lid of the eye; determining, based on the history of movement, a characteristic of the user; determining that a current movement of at least one of the eye or the eye lid matches the characteristic of the user; and filtering sensor data from the first sensor associated with the current movement in response to determining that the current movement of at least one of the eye or the eye lid matches the characteristic of the user.

According to another aspect of the present disclosure, a method comprising receiving, by a first sensor system disposed on or in a first ophthalmic device, sensor data representing movement of an eye of a user, wherein the first ophthalmic device is disposed within or upon an eye of the user; causing, based on the sensor data, storage of a history of movement of at least one of the eye or an eye lid of the eye; determining, based on the history of movement, a characteristic of the user; determining that a current movement of at least one of the eye or the eye lid matches the characteristic of the user; and filtering sensor data from the first sensor associated with the current movement in response to determining that the current movement of at least one of the eye or the eye lid matches the characteristic of the user.

BRIEF DESCRIPTION OF THE OF THE DRAWINGS

FIG. 17C is a diagrammatic representation of an exemplary electronic system incorporated into a contact lens for detecting eyelid position in accordance with the present disclosure.

DETAILED DESCRIPTION

Figure 1:
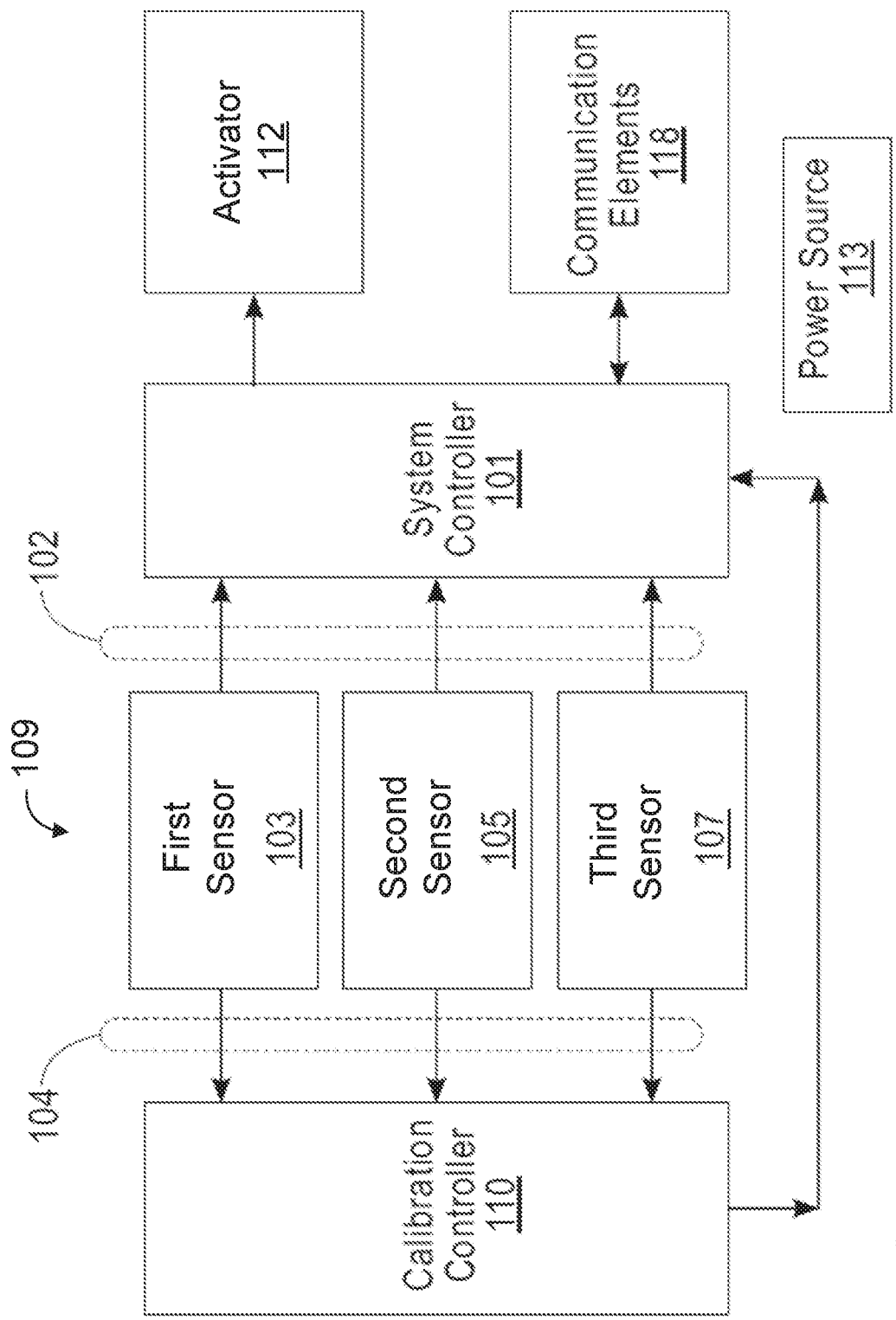
FIG. 1 shows an exemplary implementation according to an embodiment of the present disclosure.

Before explaining at least one embodiment of the disclosure in detail, it is to be understood that the disclosure is not limited in its application to the details of construction and the arrangement of the components set forth in the following description or illustrated in the drawings. The disclosure is applicable to other embodiments or of being practiced or carried out in various ways. Also, it is to be understood that the phraseology and terminology employed herein is for the purpose of description and should not be regarded as limiting. As will be appreciated by one skilled in the art, aspects of the present disclosure may be embodied as a system, method or computer program product.

The present methods and systems relate to an ophthalmic system comprising one or more ophthalmic devices, such as a system comprising at least one ophthalmic device for each eye of a user. In such a system, calibration and configuration of the one or more ophthalmic devices may be useful to ensure that a user receives assistance from the one or more ophthalmic devices at appropriate times. Calibration may be based on a history of movement of the eye (e.g., or other part of the user, such as eye lid). The history of movement of the eye may be used to determine characteristics of the user. The history of movement of the eye may be used to adjust settings, such as user defined settings (e.g., parameters), thresholds (e.g., an accommodation threshold, a gaze threshold). The history of movement of the eye may be used to filter out movements of the user, such as microsaccades movements and involuntary blinking. The history of movement of the eye may be used to determine whether to change an operational mode of the one or more ophthalmic devices. For example, the history of movement of the eye may be used to determine to change to a near mode (e.g., accommodation mode), a normal mode (e.g., unassisted viewing), and/or far mode (e.g., gaze mode).

As an illustration, because everyone's eyes are a bit different, (e.g., pupil spacing and location, lens-on-eye position, etc.), even at a fixed close distance, initial vergence angles will differ from patient to patient. It is important once ophthalmic devices (e.g., lenses) are placed in or on the eye to calibrate what the initial vergence angle is, so that differences in this angle can be assessed while in service. This value can be used for subsequent calibration calculations. In addition to these physical characteristics of the user, the system may perform calibration, filtering, and/or the like based on a history of movement of the eye of the user. The history of movement may be used to determine characteristics of the user, such as dwell characteristics or other movements. These characteristics of the user may be used to updated, refined, modify, and/or the like calibration values set based on an initial calibration process and/or value input by the user.

Figure 3:
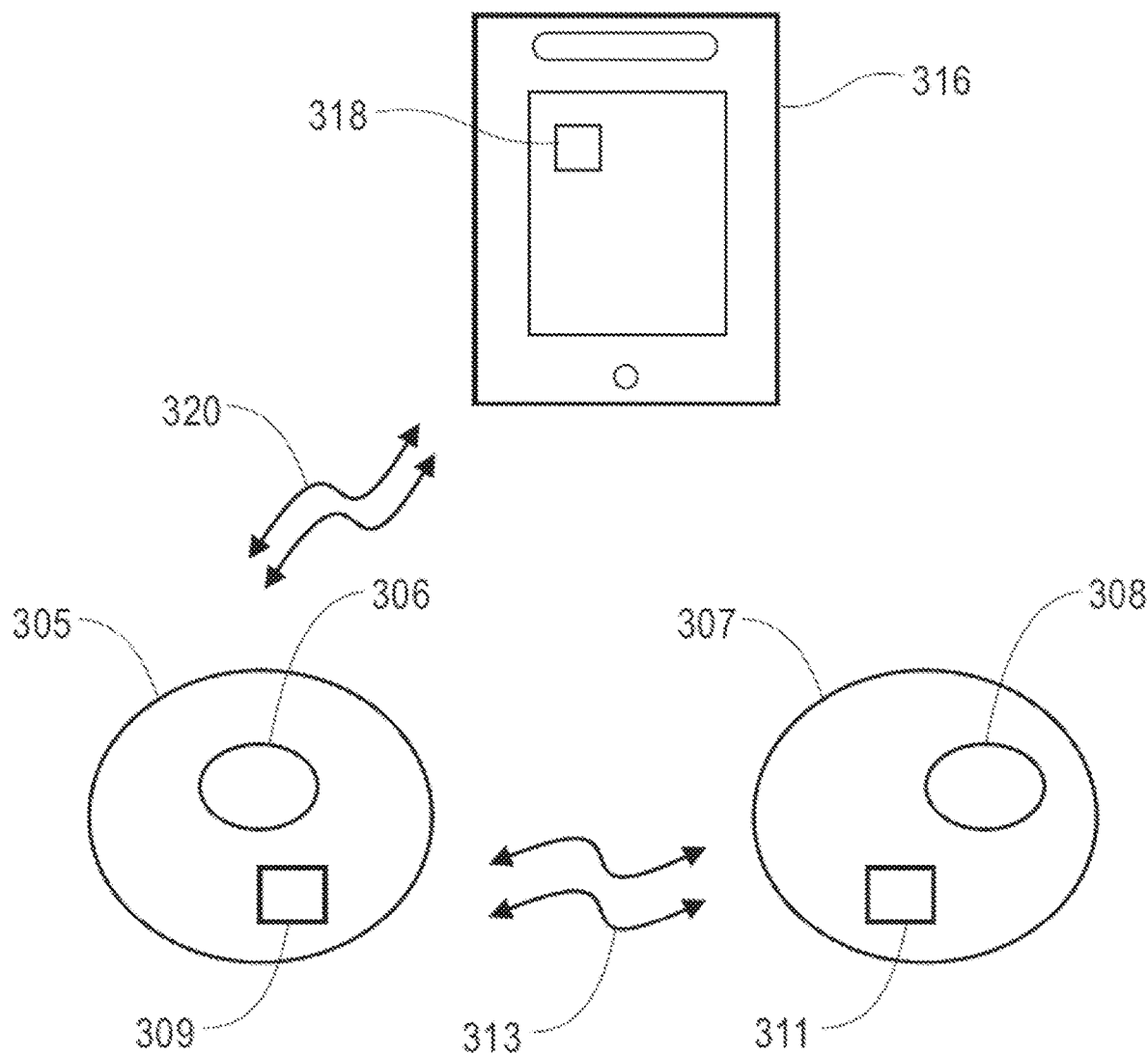
FIG. 3 shows another exemplary implementation according to an embodiment of the present disclosure.
Figure 4:
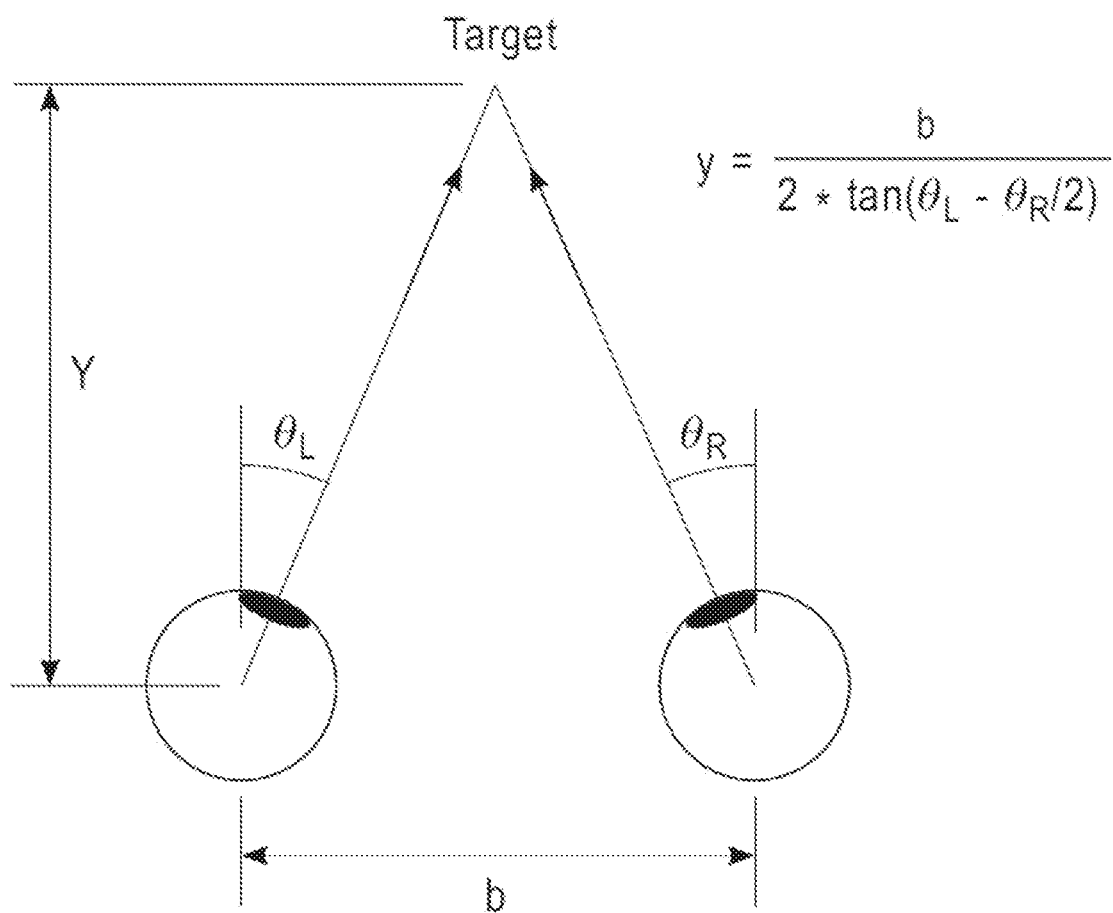
FIG. 4 shows an example of focus determination.

Now referring to FIG. 1, an exemplary implementation shows a system (e.g., sensor system) according to an embodiment of the present disclosure. The system can be disposed in or on an ophthalmic device. The ophthalmic device can comprise a contact lens or an implantable lens, or a combination of both. The ophthalmic device can be configured to be disposed within or upon an eye of a user. Disposition upon the eye may comprise being in contact with a surface of the eye, being disposed in a liquid in contact with the eye, resting on the eye, being disposed between the eye and an eyelid, and/or the like. The contact lens comprises a soft or hybrid contact lens. The ophthalmic device can be part of a system of at least two ophthalmic devices, as shown in FIG. 3.

A system controller 101 controls an activator 112 (e.g., lens activator) that changes the adaptive optics/powered lens (see FIG. 3) to control the ability to see both near and far items in focus. The system controller 101 may comprise a processor, memory, and/or the like. The system controller 101 (e.g., the processor) may be operably coupled to a sensor element 109. The system controller 101 may receive signals 102 (e.g., data signals, control signals) from the sensor system 109.

The sensor element 109 can comprise a plurality of sensors (103, 105 and 107). Examples of sensors can comprise a multidimensional sensor, a capacitive sensor, an impedance sensor, an accelerometer, a temperature sensor, a displacement sensor, a neuromuscular sensor, an electromyography sensor, a magnetomyography sensor, a phonomyography, or a combination thereof. The plurality of sensors (103, 105 and 107) can comprise a lid position sensor, a blink detection sensor, a gaze sensor, a divergence level sensor, an accommodation level sensor, a light sensor, a body chemistry sensor, neuromuscular sensor, or a combination thereof. The plurality of sensors (103, 105 and 107) can comprise one or more contacts configured to make direct contact with tear film of an eye of the user.

As an illustration, the plurality of sensors (103, 105 and 107) can comprise a first sensor 103, such as a first multidimensional sensor that includes an X-axis accelerometer. The plurality of sensors (103, 105 and 107) can comprise a second sensor 105, such as a second multidimensional sensor that includes a Y-axis accelerometer. The plurality of sensors (103, 105 and 107) can comprise a third sensor 107, such as a third multidimensional sensor that includes a Z-axis accelerometer. The plurality of sensors (103, 105 and 107) further provide calibration signals 105 to a calibration controller 110. The calibration controller 110 conducts a calibration sequence based on the calibration signals from the plurality of multidimensional sensors (103, 105 and 107) as a result of user actions which is sensed by the plurality of multidimensional sensors (103, 105 and 107) and provides calibration control signals to the system controller 101. The system controller 101 further receives from and supplies signals to communication elements 118. Communication elements 118 allow for communications between user lens and other devices such a near-by smartphone. A power source 113 supplies power to all of the above system elements. The power source can comprise a battery. The power sources may be either a fixed power supply, wireless charging system, or may be comprised of rechargeable power supply elements. Further functionality of the above embedded elements is described herein.

As another embodiment, the three axis accelerometers can be replaced by a three-axis magnetometer. Calibration would be similar because each axis would potentially require calibration at each extreme of each axis.

In the context of using sensors to determine vergence, specifically accelerometers, there are opportunities to calibrate. Offsets, due to the micro-electromechanical systems (MEMS) and/or due to the electronics, mounting on the interposer, etc. can cause variations with the algorithms and thus cause some errors in the measurement of vergence. In addition, human anatomy from person to person, is different. For instance, eye to eye space can vary from 50 to 70 mm and can cause a change in trigger points based on eye spacing alone. So there is a need to take some of these variables out of the measurement, thus calibration and customization performed by the current embodiment when the lens are on the user. This serves to improve the user experience by both adding the preferences of the user and to reduce the dependencies of the above-mentioned variations.

The plurality of sensors (103, 105 and 107) can measure acceleration both from quick movements and from gravity (9.81 m/s$^2$). The plurality of sensors (103, 105 and 107) usually produce a code that is in units of gravity (g). The determination of vergence depends on the measurement of gravity to determine position, but other methods may depend on the acceleration of the eye. There are going to be differences and inaccuracies that will require base calibration before use calibration.

The current embodiment uses three sensors on each ophthalmic device. However, calibration may be done using two sensors, e.g., the first sensor 103 (e.g., X-axis accelerometer) and the second sensor 105 (e.g., Y-axis accelerometer). In either embodiment, each accelerometer has a full scale plus, full scale minus, and zero position. The errors could be offset, linearity, and slope errors. A full calibration would calibrate to correct all three error sources for all of axes sensors being used.

One way to calibrate the sensors is to move them such that each axis is completely perpendicular with gravity, thus reading 1 g. Then the sensor would be turned 180 degrees and it should read −1 g. From two points, the slope and intercept can be calculated and used to calibrate. This is repeated for the other two sensors. This is an exhaustive way of calibrating the sensors and thus calibrating the vergence detection system.

Another way is to reduce the calibrate effort for the lens is to have the wearer do just one or two steps. One way is to have the wearer look forward, parallel to the floor, at a distance wall. Measurements taken at this time can be used to determine the offset of each axis. Determining the offset for each axis in the area where the user will spend most of the time provides a greater benefit to maintain accuracy.

Given that everyone is a little different, customizable features can prove a better user experience for all users than a one size fits all approach. When using the lens with just two modes, accommodation and gaze, then the point where this is a switch from gaze to accommodation one can have several parameters in addition to the switching threshold that would affect the user experience.

The threshold going from gaze to accommodation is depended on the user, the user's eye condition, the magnification of the lens, and the tasks. For reading, the distance between the eye and book is about 30 cm, where computer usage is about 50 cm. A threshold set for 30 cm wouldn't work well for computer work, but 50 cm would work for both. However, this longer threshold could be problematic for other tasks by activating too early, depending on the magnification and the user's own eye condition. Thus, the ability to alter this threshold, both when the lens is first inserted and at any time afterwards as different circumstances could require different threshold points, provides the user customization to improve visibility, comfort and possibly safety. Even having several present thresholds is possible and practical, where the user would choose using the interfaces described here to select a different threshold. In addition, the user could alter the threshold or other parameters by re-calibrating per the embodiments of the present disclosure as described hereafter.

Still referring to FIG. 1, switching from gaze to accommodation, the system uses the threshold as the activation point. However, going from accommodation to gaze the threshold is shifted to a greater distance, which is called hysteresis. Hysteresis is added in order to prevent uncertainty when the user is just at the threshold and there are small head movements which may cause it to switch from gaze to accommodation to gaze, etc., a behavior known as chatter. Most likely, the user will be looking at a distant target when he wants to switch, so the changing of the threshold is acceptable. The hysteresis value can be determined in several ways: one, the doctor fitting the lenses can change it, two, the user can change this value via a lens interface, and three, an adaptive algorithm can adjust it based on the habits of the user.

Custom Modes are common now in cars, i.e. sport, economy, etc. which allow the user to pick a mode based on anticipated activity where the system alters key parameters to provide the best experience. Custom Modes are also integrated into the lens of the current embodiments. Calibration and customization settings can be optimized for a given mode of operation. If the user is working in the office, it is likely that the user will need to go between states (gaze and accommodation), or even between two different vergence distances because of the nature of the tasks. Changes in the threshold, hysteresis, noise immunity, and possible head positions would occur to provide quicker transitions, possible intermediate vergence positions, and optimization for computer tasks, as well as, tasks that there is a lot if switching between gaze and accommodation. Thus, options to switch the lens into different modes to optimize the lens operation can provide an enhanced user experience. Furthermore, in an "Exercise" mode, the noise filtering is increased to prevent false triggering and additional duration of positive signal is required before switching to prevent false switching of the lens being triggered by stray glances while running. A "Driving" mode might have the lens being configured for distant use or on a manual override only. Of course, various other modes that could be derived as part of the embodiments of the present disclosure.

In today's world, the smart phone is becoming a person's personal communications, library, payment device, and connection to the world. Apps for the smartphone cover many areas and are widely used. One possible way to interact with the lens of the present disclosure is to use a phone app. The app could provide ease of use where written language instructions are used and the user can interact with the app providing clear instructions, information, and feedback. Voice activation options may also be included. For instance, the app provides the prompting for the sensor calibrations by instructing the user to look forward and prompting the user to acknowledge the process start. The app could provide feedback to the user to improve the calibration and instruct the user what to do if the calibration is not accurate enough for optimal operation. This would enhance the user experience.

Additional indicators, if the smart phone was not available, can be simple responses from the system to indicate start of a calibration cycle, successful completion, and unsuccessful completion. Methods to indicate operation include, but are not limited to, blinking lights, vibrating haptics drivers, and activating the lens. Various patterns of activation of these methods could be interpreted by the user to understand the status of the lens. The user can use various methods to signal the lens that he/she is ready to start or other acknowledgements. For instance, the lens could be opened and inserted into the eyes awaiting a command. Blinks or even closing one's eyes could start the process. The lens then would signal the user that it is starting and then when it finishes. If the lens requires a follow-up, it signals the user and the user signals back with a blink or eye closing.

The system controller 101 can be configured to perform adaptive algorithms. The adaptive algorithms may be configured to modify settings, threshold, calibration data, filtering operations and/or the like based on a history of movement of the user (e.g., movement of one or more eyes of the user). For example, the system may comprise at least two ophthalmic devices, as shown later in FIG. 3. For purposes of illustration multiple ophthalmic devices are described, one or more (or each) of which can be an ophthalmic device as shown in FIG. 1. For example, a first ophthalmic device can be configured to be disposed upon a first eye of a user. As illustrated in FIG. 1, the first ophthalmic device can comprise a first sensor system. The first sensor system can comprise a first sensor and a first processor operably connected to the first sensor. A second ophthalmic device can be configured to be disposed upon a second eye of the user. The second ophthalmic device can comprise a second sensor system. The second sensor system can comprise a second sensor and a second processor operably connected to the second sensor. Each of the at least two ophthalmic devices may be configured to perform the adaptive algorithm. One of the at least two ophthalmic devices may be configured to perform the adaptive algorithm. The at least two ophthalmic devices may be configured to take turns performing the adaptive algorithm. The at least two ophthalmic devices may be configured to perform the adaptive algorithm together.

An accommodation threshold may be defined for in a variety of ways, such as presetting the threshold of which the accommodation would be activated. Eye to eye spacing of various users may cause a small change in the accommodation threshold among users. This variation may be corrected by the doctor and/or some customization software which would upload the correction factor for the individual user. Another method adjusts an accommodation threshold while an ophthalmic device is on the user based on instructions from the user. The method automatically takes in account several variables including user preference, eye distance, eye position, lens position to create a custom threshold for the user. The user knows the accommodation threshold that he/she set and adapts their behavior accordingly. The user can further modify the accommodation threshold for changing circumstances to better fit the current activity, if necessary.

The present methods and systems may be used to add adaptive (e.g., automatic) adjustment to the accommodation threshold to enhance the user's experience by fine tuning the threshold by observing the habits of the user. Observation of dwell time vs. distance might prove to be confounding to the user and be "too helpful." For example, if the user has been reading for a while (e.g., a preset time period) at 30 cm and then the user wants to use the computer at 50 cm, the threshold may have been previously adjusted to 30 cm and thus, does not activate at 50 cm. In this situation, the user may: 1) wait, staring at the screen until the ophthalmic device determines that the user really wants to see at 50 cm or 2) move view distance to 30 cm (manually adjusting to accommodation mode). These choices may be improved upon using adaptive algorithms. Alternatively, the user may look closer than the near threshold to have the system switch, then revert to the desired viewing distance. The near to far (accommodation-to-gaze, or rising distance) threshold may be further away than 50 cm to allow use of the accommodation mode for a 50 cm distance. This is the hysteresis provided by having two thresholds: far-to-near and near-to-far.

In some implementations, the accommodation threshold may be a single point threshold or binary switch where once reached, the ophthalmic devices are activated. For a good user experience, the following conditions may be met: the lenses are needed and activated, or not needed and deactivated. Both other cases are not desirable, i.e., not needed and activated or needed and not-activated. Thus, the accommodation threshold may be adjusted to prevent the latter two scenarios. For instance, the previous example shows that a static accommodation threshold may have resulted in the user being in undesirable scenarios, but a simple accommodation threshold at some distance further than 50 cm, e.g. 55 cm, would work for the 30 cm book reading position and the 50 cm computer screen reading position.

Adaptive algorithms may be used to achieve an optimal accommodation threshold. The optimal accommodation threshold may be at just beyond the longest distance that the user needs the magnification and no longer than necessary to prevent the ophthalmic device from being Active while the ophthalmic device is not needed.

The ophthalmic system may receive the information that the user customized, e.g., a user defined threshold. The ophthalmic system may monitor where the user activates the accommodation by exceeding that user defined accommodation threshold. The ophthalmic system may determine if the user dwells (e.g., looks as a fixed distance) at exactly the accommodation threshold or if the user dwells at a different distance, such as a longer distance than the accommodation threshold. The adaptive system may add or subtract distance to the accommodation threshold and/or some additional Hysteresis since the user usually uses ophthalmic device at the longest distance.

The adaptive algorithm may update the accommodation threshold based on user input. For example, if the user started dwelling at 60 cm, it may be difficult to determine if the user desired to activate the ophthalmic device. If a user is reading, it may be difficult to determine whether the accommodation threshold should be adjusted to 30 cm. User input may be used to determine if a user dwelling at a specific distance should be used as a basis to adjust the accommodation threshold. The user may communicate with the one or more ophthalmic devices by a gesture, voice command, entering a command via a user interface (e.g., mobile phone, computer, tablet). The user may communicate that the user rejects a particular adjustment of the accommodation threshold. As an illustration, a user may view slightly past the threshold to cause activation, then may dwell at a distance not quite at the threshold. If this distance is more than, e.g., 10 or 15% of the range away from the threshold then it may be more comfortable for the user to move the threshold closer to the dwell distance. However, a certain time period at a dwell distance may be used as a trigger to adjust accommodation.

Adaptive algorithms may be implemented in a system where the one or more ophthalmic devices determined that a user wanted to accommodate and the system tracked and adapted to the longest distance threshold for accommodation.

Adaptive algorithms may be implemented to adjust user defined threshold to work better with the actual habits of the user. Small changes to threshold and hysteresis may be made to prevent chattering. The system may be configured to ignore or be slower to react to sudden changes after a long period of fixation.

Adaptive algorithms may be implemented to filter (e.g., reject, ignore) user behavior. For example, involuntary blink rate may be determined. Each user may have unique blink habits, the system can adapt to filter and/or reject these false signals. The system may be used for microsaccades filtering, e.g., filtering small movements made by the eye of the user.

Adaptive algorithms may be used to modify multiple accommodation thresholds. For example, accommodation thresholds may comprise a gaze threshold for transitioning from accommodation to gaze (e.g., or activating gaze from being deactivated) and an accommodation threshold for transitioning from gaze to accommodation (e.g., or activating accommodation from being deactivated).

The system may be configured to store adaptive algorithm data (e.g., the history of movement of user, any adjustments made for certain situations, and/or the like). The adaptive algorithm data may be stored on local memory of the one or more ophthalmic devices. The adaptive algorithm data may be transmitted to and stored on a remove device, such as a user device (e.g., mobile phone), a remote server, and/or the like.

Figure 6:
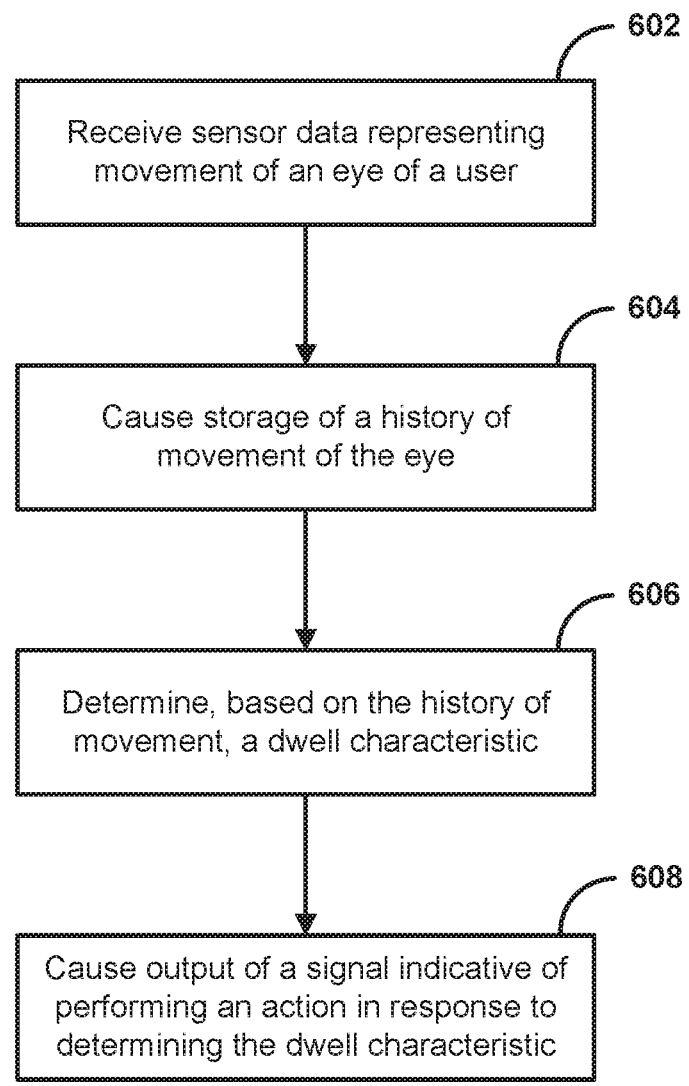
FIG. 6 shows another flowchart according to an embodiment of the present disclosure.
Figure 7:
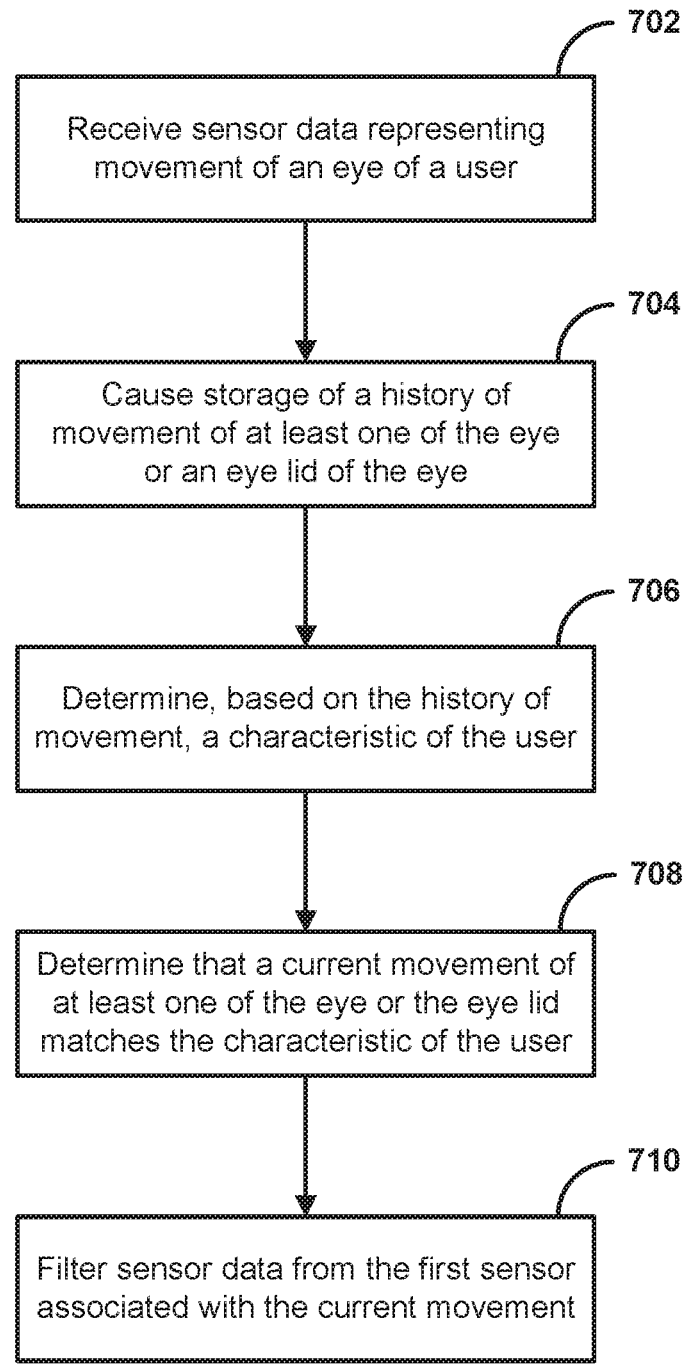
FIG. 7 shows another flowchart according to an embodiment of the present disclosure.

The system controller 101 can be configured to perform adaptive algorithms. For example, system controller 101 may be configured to perform the methods disclosed in FIG. 6 and FIG. 7. The system controller 101 may be configured to receive sensor data from one or more sensors of a sensor system. The sensors data may represent one or more movements of the user (e.g., movements of the eye of the user). The sensor data may be stored as part of a history of movements of the user. The sensor data and/or history of movements of the user may be used to determine one or more characteristics of the user. The one or more characteristics may be used to modify a threshold, a setting, a parameter, a calibration configuration, signal filtering, and/or the like. The one or more characteristics may change over time and in different contexts as the history of movements changes over time. Patterns in the sensor data, the history of movements, the determined characteristics, and/or the like may be determined. For example, the patterns may be determined based on machine learning. As shown in FIG. 6, an accommodation threshold may be adjusted based on the history of movements of the user. However, other thresholds and parameters may be adjusted based on the history of movements. For example, as shown in FIG. 7, sensor data may be filtered based on a history of movement of the user.

Figure 2:
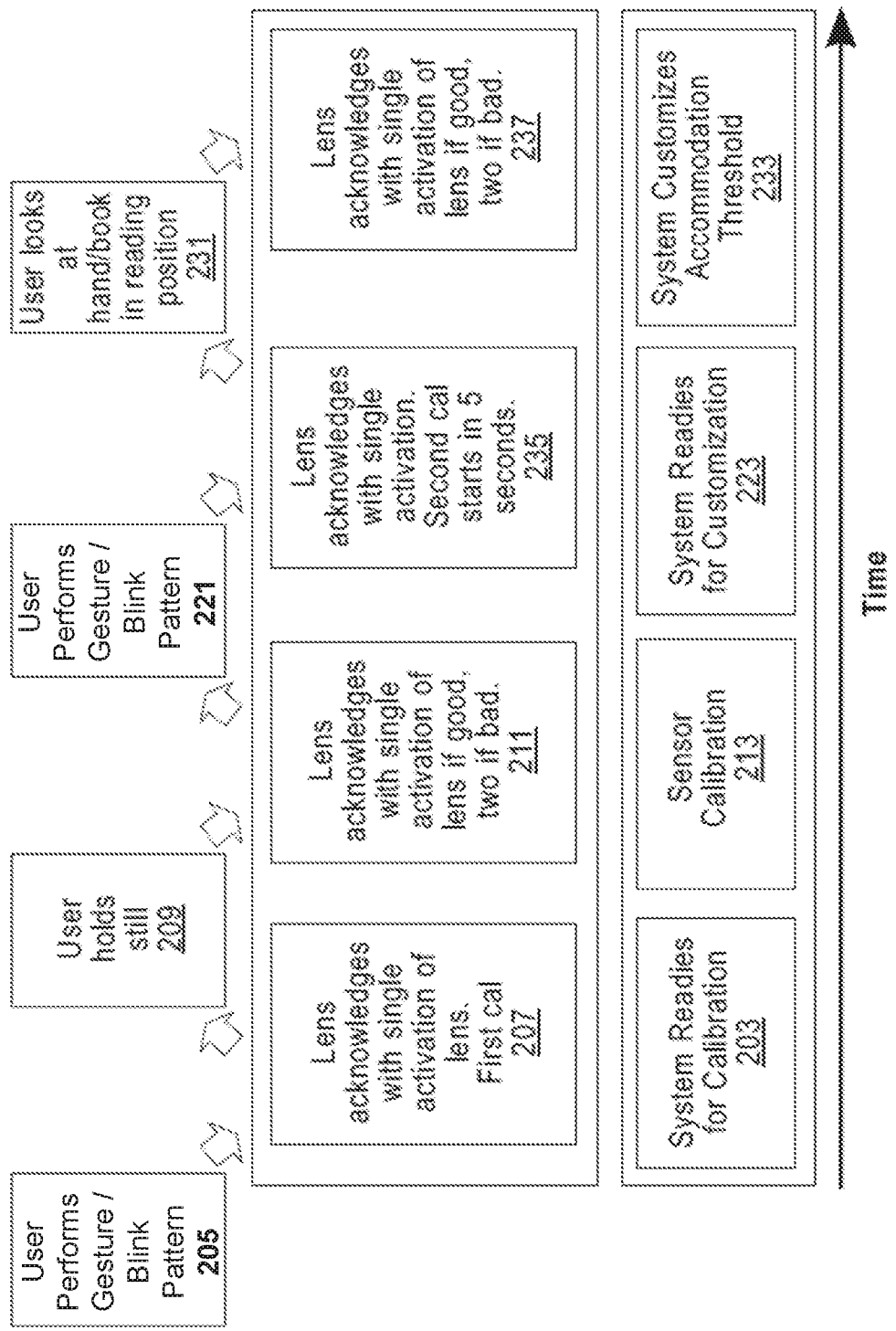
FIG. 2 shows a flowchart according to an embodiment of the present disclosure.

Referring to FIG. 2, one method according to an embodiment of the present disclosure is depicted. The process starts at an initial time (far left of the figure) and proceeds forward in time. Once the lens (see FIG. 3) are inserted, the system readies for calibration 203. The user performs a blink pattern 205. The lens acknowledges with a single activation of the lens 207 as part of a first calibration. The user holds still 209 as the system and the sensor calibration 213 starts. The lens acknowledges with a single activation of the lens if the first stage of calibration is good 211. If the initial calibration is bad, then the lens acknowledges with a double activation 211. If the calibration is bad, then the user must restart the calibration process 205. After the initial calibration, the system is ready for customization 223. The user conducts another blink pattern 221. The lens acknowledges with a single activation of the lens and a second calibration, customization, is started in some fixed time 235 as part the system customization accommodation threshold 233. The user then looks at either their hand or a book at reading position 231. The lens acknowledges with a single activation of the lens if the second stage of calibration customization is good 237. If the second stage of calibration customization is bad, then the user must restart the calibration customization process 221. Once the lens acknowledges with a single activation of the lens that the second stage of calibration customization is good 237 the system has the completed customization accommodation calibration and the lens is ready for full use by the user. The ophthalmic devices may continue to refine the accommodation threshold after the accommodation threshold is customized based on the calibration. For example, the adaptive algorithms described herein may be used to adjust the accommodation threshold based on a history of movement of the user (e.g., movement of one or more eyes of the user).

Other embodiments to customize the threshold can be accomplished. One way is to have the user's doctor determine the comfortable distance for the user by measuring the distance between the eyes of the patent, the typical distance for certain tasks, and then calculate the threshold. From there, using trial and error methods, determine the comfortable distance. Various thresholds can be programmed into the lens and the user can select the task appropriate threshold.

Another method is to allow the user to select his threshold himself. The lens can use the same system that it uses to measure the user's relative eye position to set the accommodation threshold. Where the user's preference of when to activate the extra lens power. There is an overlap where the user's eyes can accommodate unassisted to see adequately and where the user's eyes also can see adequately with the extra power when the lens is active. At what point to activate determined by user preference. Providing a means for the user to set this threshold, improves the comfort and utility of the lenses. The procedure follows this sequence:

The user prompts the system to start the sequence. Initially the system could prompt the user as a part of the initial calibration and customization;

The lenses are activated. The ability to achieve a comfortable reading position and distance requires the user to actually see the target, thus the lens are in the accommodation state;

The user focuses on a target which is at a representative distance while the system determines the distance based on the angles of the eyes by using the sensor information (accelerometers or magnetometers); after several measurements and noise reduction techniques the system calculates a threshold and indicates that it has finished, The new threshold has been determined. A slight offset is subtracted to effectively place the threshold a little farther away, thus creating hysteresis. This is necessary to move the threshold slightly longer (angle slightly lower) in order to guarantee when the user is in the same position, the system will accommodate even with small head or body position differences; The value of this hysteresis could be altered by an algorithm that adapts to user habits. Also, the user could manually change the value if the desired by having the system prompt the user to move the focus target to a position that the user does not want the lenses to activate all the while focusing on the target. The system would deactivate the lenses and then determine this distance. The Hysteresis value is the difference in the deactivate distance and the activate distance. Lenses are now on dependent on the new threshold and hysteresis values. The ophthalmic devices may continue to refine the accommodation threshold after the user has customized the accommodation threshold. For example, the adaptive algorithms described herein may be used to adjust the accommodation threshold based on a history of movement of the user (e.g., movement of one or more eyes of the user).

To have a good user experience, the user can receive confirmation that the system has completed any adjustments or customization. In addition, the system can be configured to determine if the user performed these tasks properly and if not, and then request that the user preforms the procedure again. Cases that prevent proper customization and adjustment may include excessive movement during measurement, head not straight, lens out of tolerance, etc. The interactive experience will have far less frustrated or unhappy users.

Feedback can be given through various means. Using a phone app provides the most flexibility with the screen, cpu, memory, internet connection, etc. The methods as discussed for calibration per the embodiments of the present disclosure can be done in conjunction with the use of a smartphone app with use of the communication elements as described in reference to FIG. 1 and with reference to FIG. 3 hereafter.

As a part of continual improvement for the lens, data for the ophthalmic devices can be collected and sent back to the manufacturer (anonymously) via the smartphone app to be used to improve the product. Collected data includes, but not limited to, accommodation cycles, errors, frequency that poor conditions occur, number of hours worn, user set threshold, etc.

Other methods to indicate operation include, but not limited to, blinking lights, vibrating haptics drivers, and activating the ophthalmic devices. Various patterns of activation of these methods could be interpreted by the user to understand the status of the ophthalmic device.

Referring now to FIG. 3, shown is another exemplary implementation according to an embodiment of the present disclosure in which sensing and communication may be used to communicate between a pair of ophthalmic devices (305, 307), such as contact lenses. Pupils (306, 308) are illustrated for viewing objects. The ophthalmic devices (305, 307) include embedded elements, such as those shown in FIG. 1. The embedded elements (309, 311) included for example 3-axis accelerometers/magnetometers, lens activators, calibration controller, a system controller, memory, power supply, and communication elements as is described in detail subsequently. A communication channel 313 between the two ophthalmic devices (305, 307) allows the embedded elements to conduct calibration between the ophthalmic devices (305, 307). Communication may also take place with an external device, for example, spectacle glasses, key fob, dedicated interface device, or a smartphone.

Communication between the two ophthalmic devices (305, 307) can be performed in order to update settings (e.g., threshold), communicate a history of sensor data, and/or the like. The ophthalmic devices (305, 307) can periodically communicate data, such as sensor data, output of calculations (e.g., characteristic of a user), parameter data (e.g., filters applied). Communication between the two ophthalmic devices (305, 307) can be periodically performed, such as a predefined number of times during a time period, according to specific schedule, in response to a triggering condition, and/or the like.

As an example, communication between the ophthalmic devices (305, 307) can be important to detect proper calibration. Communication between the two ophthalmic devices (305, 307) may take the form of absolute or relative position, or may simply be a calibration of one lens to another if there is suspected eye movement. If a given ophthalmic device detects calibration different from the other ophthalmic device, it may activate a change in stage, for example, switching a variable-focus or variable power optic equipped contact lens to the near distance state to support reading. Other information useful for determining the desire to accommodate (focus near), for example, lid position and ciliary muscle activity, may also be transmitted over the communication channel 313. It should also be appreciated that communication over the channel 313 could comprise other signals sensed, detected, or determined by the embedded elements (309, 311) used for a variety of purposes, including vision correction or vision enhancement.

The communications channel (313) comprises, but not limited to, a set of radio transceivers, optical transceivers, or ultrasonic transceivers that provide the exchange of information between both lens and between the lenses and a device such as a smart phone, FOB, or other device used to send and receive information. The types of information include, but are not limited to, current sensor readings showing position, the results of system controller computation, synchronization of threshold and activation. In addition, the device or smart phone could upload settings, sent sequencing signals for the various calibrations, and receive status and error information from the lenses.

Still referring to FIG. 3, the ophthalmic devices (305, 307) further communicate with a smart phone (316) or other external communication device. Specifically, an app 318 on the smart phone (316) communicates to the ophthalmic devices (305, 307) via a communication channel (320). The functionally of the app (318) follows the process as outlined with referenced to FIG. 5 (described hereafter) and instructs the user when to perform the required eye movements. In addition, the device or smart phone (316) could upload settings, sent sequencing signals for the various calibrations, and receive status and error information from the contact lenses (305, 307).

Figure 5:
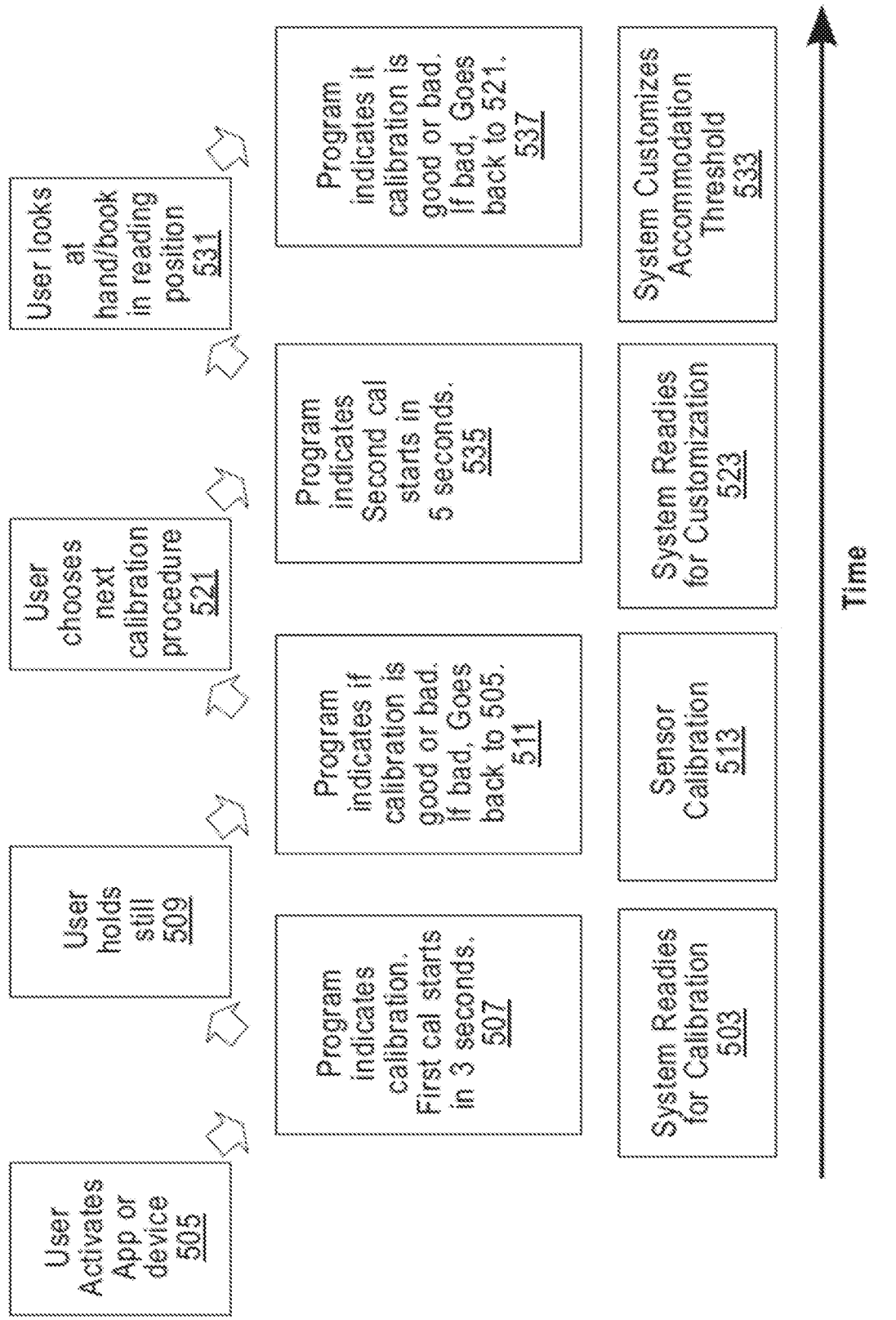
FIG. 5 shows another flowchart according to an embodiment of the present disclosure.

Referring to FIG. 5, another method according to an embodiment of the present disclosure is depicted. The process starts at an initial time (far left of the figure) and proceeds forward in time. Once the ophthalmic devices (see FIG. 3) are inserted, the system readies for calibration 503. User activates App or device 205. The app program indicates calibration and the first calibration starts in 3 seconds 507 as part of a first calibration. The user holds still 509 as the system and the sensor calibration 513 starts. The program indicates if calibration is good or bad 511. If calibration is bad the program restarts and goes back (to step 505) 511. After the initial calibration, the system is ready for customization 523. The user chooses the next calibration procedure 521. The program indicates the second calibration will start in 5 seconds 535 as part the system customization accommodation threshold 533. The user then looks at either their hand or a book at reading position 531. The program determines if second stage of calibration customization is good 537. If the second stage of calibration customization is bad, then the user must restart the calibration customization process 521. Once the program acknowledges that the second stage of calibration customization is good 537 the system has the completed customization accommodation calibration and the lenses are ready for full use by the user. The ophthalmic devices may continue to refine the accommodation threshold after the accommodation threshold is customized based on the calibration. For example, the adaptive algorithms described herein may be used to adjust the accommodation threshold based on a history of movement of the user (e.g., movement of one or more eyes of the user).

In reference to FIG. 6, and by way of further explanation, an ophthalmic system may be configured to perform the following operations to implement an adaptive algorithm.

At step 602, sensor data representing movement of an eye of a user, may be received. The sensor data may be received by a first sensor system disposed on or in a first ophthalmic device. The first ophthalmic device may be disposed upon or within an eye of the user. The first ophthalmic device may comprise a contact lens or an implantable lens, or a combination of both. The sensor data may comprise data from a vibration sensor, a capacitance sensor, an impedance sensor, an accelerometer, a combination thereof, and/or the like. For example, the sensor data may comprise eye movement, eyelid movements, eyelid position, eye position, eye muscle position, eye muscle movements, eye vergence, eye acceleration, speed and/or direction of eye movements, a combination thereof, and/or the like. Example sensors for detection of the sensor data are described further herein.

At step 604, storage of a history of movement of the eye may be caused. Causing storage of the history of movement of the eye may comprise causing storage in a local storage of the first sensor system. Causing storage of the history of movement of the eye may comprise causing storage in remote storage external to first sensor system. The remote storage may comprise a mobile device, a remote server, a tablet, a computing station, and/or the like.

At step 606, a dwell characteristic may be determined. The dwell characteristic may indicate a distance at which the eye is fixated when an event occurs. The eye being fixated may comprise the eye being focused on objects within distance range (e.g., up close, far way). The eye may continue to move (e.g., reading words of a book) when fixated, such as when the eye moves to observe objects within the distance range. The dwell characteristic may be determined based on the history of movement. The event may comprise activating (e.g., changing the adaptive optics from one focus to another focus) the first ophthalmic device. The event may comprise the eye remaining fixated at the distance for a minimum amount of time. The dwell characteristic may comprise an activity (e.g., or context) associated with dwelling at a distance. For example, the activity may comprise a user activity, such as watching television, reading a booking, driving a car, working, running, walking, and/or the like. The sensor data may be used to determine the activity. Accelerometer values may indicate that the user is moving eyes side to side, indicating a reading motion. A range of eye movement may be determined. Different ranges of eye movement may be associated with different activities. Different distances at which the eye is fixated may be associated with different activities. As an example, a certain dwell could indicate reading, which thus indicates a distance within a certain range (e.g., thus triggering a focus change).

The sensor data from a variety of sensors may be used to more accurately determine when to cause output of a signal indicative of performing an action (e.g., to change a parameter), and/or what activity a user is engaged in. For example, a voting scheme may be used in which different data and/or sensors may be given different weights in making a determination. The weighting may vary depending on the context. For example, several sensors may generate data indicative of the same activity, such as reading a book. First sensor data from one sensor may indicate that a user's eye is fixated at a distance close to the user. Second sensor data from another sensor may indicate that the user is not moving the eye back and forth, suggesting that the user is not reading. The second sensor data may be given more weight in a determination of whether to adjust an accommodation threshold, and/or determine whether the user is reading a book or not.

At step 608, an output of a signal indicative of performing an action may be caused. Output of the signal indicative of performing the action may be caused based on (e.g., in response to) determining the dwell characteristic.

Causing output of the signal indicative of performing the action may comprise causing adjustment of a parameter. The parameter may comprise a threshold, such as an accommodation threshold and/or a gaze threshold. The threshold may be a threshold for enabling a viewing mode, such as a near viewing mode (e.g., accommodation mode), a far viewing mode (e.g., a gaze mode). The accommodation threshold may comprise a threshold for activating an ophthalmic device (e.g., or a lens of an ophthalmic device) to perform accommodation operation. The accommodation threshold may comprise a distance threshold indicative of a minimum or maximum distance at which the eye is fixated before activating the ophthalmic device (e.g., the lens) to perform the accommodation operation. The activation of the lens may comprise activation by the user, activation by the ophthalmic device (e.g., based on analysis of sensor data), receiving an instruction for activation, and/or the like. The accommodation threshold may comprise a time threshold indicative of a minimum time at which the eye is fixated at a distance before activating the lens to perform the accommodation operation. The accommodation operation may comprise adjusting (e.g., activating, turning on) the ophthalmic device (e.g., or lens) to allow the eye to focus at a distance.

Figure 8:
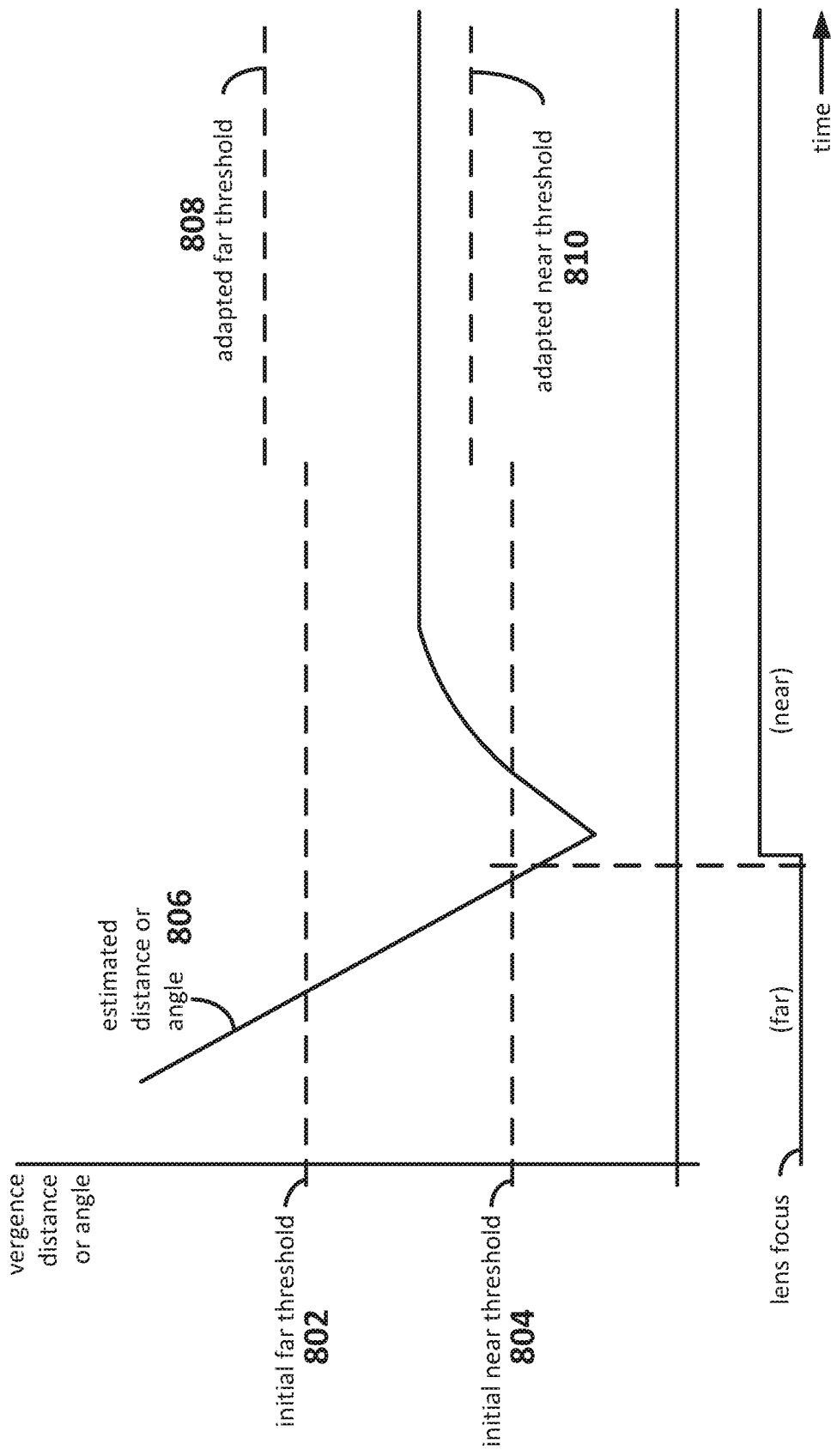
FIG. 8 is a graph illustrating adjustment of a parameter of an ophthalmic device.

Causing adjustment of the parameter may comprise increasing or decreasing the parameter (e.g., a value of an accommodation threshold, a value of a gaze threshold). For example, the accommodation threshold and/or gaze threshold may be increased from a first distance to a second distance (e.g., as shown in FIG. 8). The second distance may be farther from the user than the first distance.

The parameter (e.g., or value thereof) may be determined based on an instruction from the user indicating the parameter. The parameter (e.g., accommodation threshold, gaze threshold, activation threshold, deactivation threshold, hysteresis value) may comprise a user defined parameter. Causing adjustment of the parameter may comprise adjusting the user defined parameter (e.g., threshold). For example, the history of the movement of the eye and/or the dwell characteristic may not match the user defined parameter. Thus, the user defined parameter (e.g., threshold) may be increased and/or decreased as the behavior of the user changes over time.

In an aspect, input from the user associated with adjusting the accommodation threshold may be received. The input may indicate whether the user accepts or rejects the adjusting of the parameter. The dwell characteristic may be adjusted if the input indicates that the user rejects the adjusting of the parameter. For example, an accommodation threshold may be adjusted after user move his or her eye up closely at a drawing. Following adjustment, the user may indicate that the user rejects the adjustment of the accommodation threshold, as the user does not typically look closely at a drawing.

In an aspect, it may be determined that a current movement of the eye satisfies the dwell characteristic. Causing output of a signal indicative of performing an action (e.g. or adjusting an accommodation threshold or gaze threshold) may be performed in response to determining that the eye satisfies the dwell characteristic. For example, the dwell characteristic may be associated with a particular action of the user, such as reading a book, reading a computer screen, driving, playing a sport, and/or the like. The current movement may indicate that the user is performing the action. Different accommodation thresholds may be associated with different actions of the user. The ophthalmic system may be configured to adjust one or more parameters as the ophthalmic system determines that a user is engaged in a different action associated with a different parameter settings (e.g., thresholds).

In reference to FIG. 7, and as another example, an ophthalmic system may be configured to perform the following operations to implement an adaptive algorithm. At step 702, sensor data representing movement of an eye of a user may be received. The sensor data may be received by a first sensor system disposed on or in a first ophthalmic device. The first ophthalmic device may be disposed upon or within an eye of the user. The first ophthalmic device may comprise a contact lens or an implantable lens, or a combination of both.

At step 704, storage of a history of movement of at least one of the eye or an eye lid of the eye may be caused. The storage may be caused based on the sensor data. Causing storage of the history of movement of the eye may comprise causing storage in a local storage of the first sensor system. Causing storage of the history of movement of the eye may comprise causing storage in remote storage external to first sensor system. The remote storage may comprise a mobile device, a remote server, a tablet, a laptop, a computing station, and/or the like.

At step 706, a characteristic of the user may be determined. The characteristic of the user may be determined based on the history of movement. The characteristic of the user may comprise a blink rate, a microsaccades movement, a dwell characteristic, a vergence characteristic a combination thereof, and/or the like. The characteristic of the user may comprise a dwell time indicative of a minimum time that the eye is fixated at a distance before activating a lens to perform an accommodation operation.

At step 708, it may be determined that a current movement of at least one of the eye or the eye lid matches the characteristic of the user. For example, sensor data associated with a time frame (e.g., within a predefined time of the present time) may be analyzed to determine a current characteristic. The current characteristic may comprise a blink rate, a movement pattern, an eye fixation distance, vergence value, and/or the like. The current characteristic may be compared to the characteristic of the user previously determined. If the current characteristic is within a threshold similarity to the characteristic of the user previously determined, then it may be determined that the current movement matches the characteristic of the user.

At step 710, sensor data from the first sensor associated with the current movement may be filtered. The sensor data may be filtered in response to determining that the current movement of at least one of the eye or the eye lid matches the characteristic of the user. Filtering sensor data from the first sensor associated with the current movement may comprise rejecting the sensor data. Filtering sensor data from the first sensor associated with the current movement may comprise determining that the sensor data is not indicative of a command from the user. Filtering the sensor data from the first sensor associated with the current movement may comprise filtering involuntary blink movements based on the blink rate. Filtering the sensor data from the first sensor associated with the current movement may comprise filtering microsaccades movement. Filtering the sensor data from the first sensor associated with the current movement may comprise filtering movement of the eye movement that does not satisfy a dwell characteristic (e.g., a dwell time, a dwell distance).

FIG. 8 is a graph illustrating adjustment of a parameter of an ophthalmic device. An ophthalmic device may be programmed with one or more initial thresholds, such as an initial far threshold 802 and an initial near threshold 804. The initial far threshold 802 may be a threshold for enabling a far mode (e.g., gaze mode). The initial near threshold 804 may be a threshold for enabling a near mode (e.g., accommodation mode). For example, the ophthalmic device may switch from a normal mode (e.g., in which no assistance is provided to the user to see, or the device is set for viewing distances between near mode and far mode) to either the near mode or the far mode. The ophthalmic device may switch from near mode to far mode, far mode to near mode, normal mode to far mode, and/or far mode to normal mode. The threshold may be a distance threshold based an estimated distance that the eye is attempting to look or other metric based on sensor data (e.g., vergence angle, eyelid position, eye position, eye muscle position). A line 806 on the graph illustrates when a user switches from far mode to near mode. If the user passes the initial near threshold 804, the ophthalmic device modifies the refractive power of the ophthalmic lens to switch from focusing at a far distance to focusing at a near distances. Though not shown by the line 806, if the user were to change eye position to look at a threshold distance beyond the initial far threshold 802, then the ophthalmic device modifies the refractive power of the ophthalmic lens to switch from focusing at a near distance to focusing at a far distance.

The initial near threshold 804 and/or the initial far threshold 802 may be determined by a professional, user input, or be a default setting. The initial near threshold 804 and/or the initial far threshold 802 may be modified based on user behavior. For example, as shown by the line 806, the user may attempt to focus at a distance between the initial near threshold 804 and the initial far threshold 802. If the user dwells at the distance for a time period, it may be determined to modify the initial near threshold 804 and/or the initial far threshold 802. An adapted far threshold 808 and/or an adapted near threshold 810 may be determined (e.g., in response to the determination to modify the initial near threshold 804 and/or the initial far threshold 802). The adapted far threshold 808 and/or an adapted near threshold 810 may be selected to minimize switching between operation modes.

Additional information may be used to determine whether to modify the initial near threshold 804 and/or the initial far threshold 802. The additional information may be used with a dwell distance and/or dwell time to determine whether to modify the initial near threshold 804 and/or the initial far threshold 802. The additional information may comprise one or more of eye position, eyelid position, vergence angle, eye muscle movement, eye movement, and/or the like. For example, the additional information may be determined based on signals and/or data from a capacitance sensor (e.g., to detect eye position or eyelid position). The additional information may be determined based on signals and/or data from an impedance sensor. The additional information may be determined based on signals and/or data from one or more accelerometers (e.g., to determine vergence angle, eye movement, eye position).

As an illustration, the additional information may provide additional context for determining whether to perform an action, such as modifying the initial near threshold 804 and/or the initial far threshold 802. For example, it can be determined that a user is using a computer based on vibration detected by a vibration sensor due to typing, moving a mouse, and/or the like. The angle and/or distance of eye fixation may be determined by one or more of an impedance sensor, a capacitance sensor, an accelerometer, and/or the like. An accommodation threshold or other threshold associated with viewing a computer display may be adjusted to an appropriate level based on the distance of the eye fixation (e.g., thereby allowing the ophthalmic device to more accurately change operation of a lens to an appropriate setting for computer display viewing).

In an aspect, an updated hysteresis value may be determined based on the additional information, dwell time, dwell distance, a combination thereof, and/or the like. An initial hysteresis value may comprise a difference between the initial far threshold 802 and the initial near threshold 804. A determination may be made to modify the initial hysteresis value to determine an updated hysteresis value. The updated hysteresis value may comprise a difference between the adapted far threshold 808 and the adapted near threshold 810. One or more of the adapted far threshold 808 and the adapted near threshold 810 may be determined based on the updated hysteresis value.

As described herein there may be a default near-going threshold and default far going threshold, where the distance between is hysteresis. For example, in initial use a user starts at far mode, looking farther than the near-going threshold. The user may dwell at some far distance for a time. It is understood that dwell may be a point distance or may be an average or estimate based on distances over a given time. The user may then looks at an object (e.g., closer than current dwell). As an illustration, the object is farther than the near-going threshold, but the user desires activation. Thus, the user may bring the object, e.g. a hand, closer than the near-going threshold, looks at it for long enough for the system to switch to near mode (accommodation). Then the user can look at the desired object or other objects under the near mode, which may be at a distance between the near-going and far-going thresholds. Accordingly, the user may dwell at this distance.

The user may then look at an object slightly further away but closer than the far-going threshold. If they desire the system to switch to far mode, they can gaze at an even further object until the system switches to far mode. The user can then look at the second desired object for some time and the system will not switch to near mode unless they bring themselves and the object closer past the near-going threshold. Thus the user can force the system to switch to either near or far mode without any adaptation in the system. Such actions may be reordered or otherwise noted by the system and customization may be applied. For example, the "manual" system of forcing adjustment may be adapted based on learned behavior of a particular user. As an example, the system may determine that a user prefers to view near accommodation at a certain distance and may adjust thresholds or setting based on the above manual procedure.

Alternatively or additionally, an adaptive system can be constructed to modify the thresholds based on dwell distances in a given mode. Predetermined near/far scenarios may be understood (e.g., generated, stored), which may include how close the thresholds are to dwell distances, how to adapt if too far or too close, check if not too close to another dwell distance. For example, the near threshold may be moved farther for a first dwell distance but not farther than a second dwell distance that may be further out. Certain constraints may apply, such as, not allowing near/far thresholds to invert and maintain a minimum hysteresis both to avoid chatter and to allow the user to force switching and maintain a setting (near/far) for distances between the two thresholds.

Figure 9:
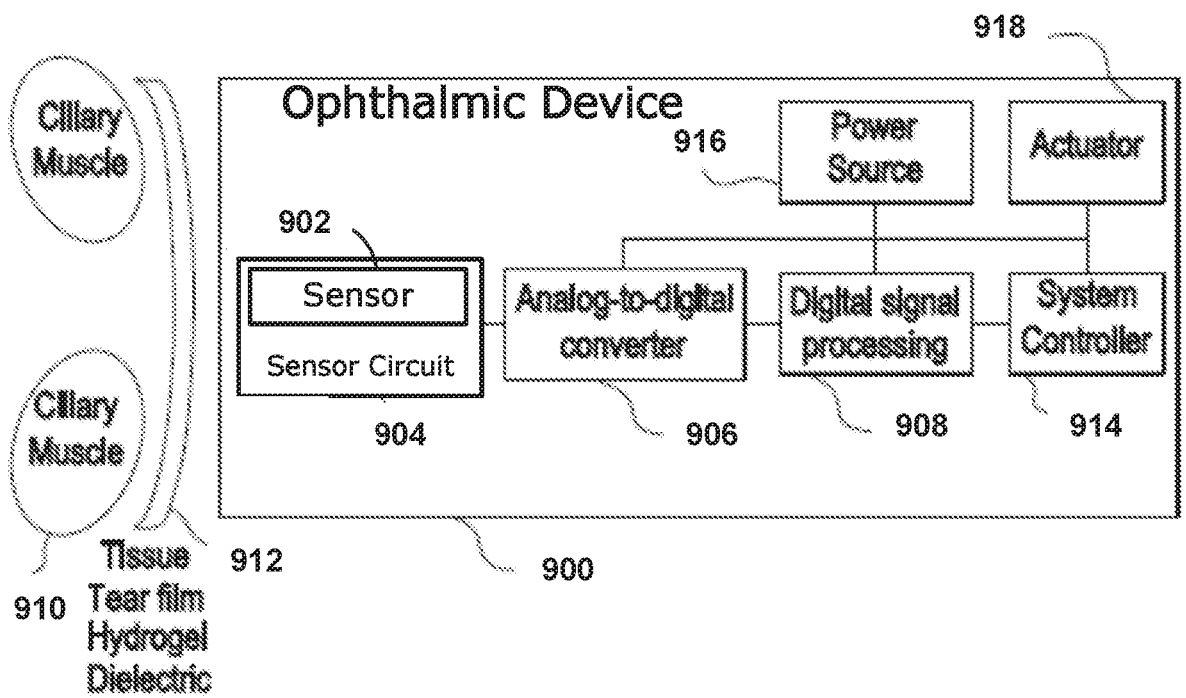
FIG. 9 illustrates an exemplary ophthalmic device comprising a sensor system in accordance with some embodiments of the present disclosure.

The following figures and description provide examples of a variety of sensors that may be used to determine dwell characteristics (e.g., dwell context, user activity) associated with a user. FIG. 9 illustrates, in block diagram form, an ophthalmic device 900 disposed on the front surface of the eye or cornea 912, in accordance with one exemplary embodiment of the present disclosure. Although the ophthalmic device 900 is shown and described as a being disposed on the front surface of the eye, it is understood that other configurations, such as those including intraocular lens configuration may be used. In this exemplary embodiment, the sensor system may comprise one or more of a sensor 902, a sensor circuit 904, an analog-to-digital converter 906, a digital signal processor 908, a power source 916, an actuator 918, and a system controller 914. As illustrated, the ciliary muscle 910 is located behind the front eye surface or cornea 912. More specifically, the globe of the eye can be divided into two segments; namely, the anterior chamber and the posterior chamber. The iris is the partition between the anterior and posterior chambers. Between the front surface of the crystalline lens and the back surface of the iris is the posterior chamber. At the base of the iris is the ciliary body which produces aqueous humor and is continuous with the ciliary muscle. The ophthalmic device 900 is placed onto the front surface of the eye 912 wherein the electronic circuitry of the sensor system may be utilized to implement the neuromuscular sensing of the present disclosure. The sensor 902 as well as the other circuitry is configured to sense signals from ciliary muscle 910 actions through the various tissue and liquids forming the eye and produced by the eye. As set forth above, the various fluids comprising the eye are good conductors of electrical and acoustical signals.

In this exemplary embodiment, the sensor 902 may be at least partially embedded into the ophthalmic device 900. The sensor 902 may be in mechanical communication with the eye, for example disposed to sense vibration associated with (e.g., translating through) the eye. The sensor 902 may be in electrical communication with the eye, for example in series with the eye (e.g., disposed to sense a change in impedance associated with the eye). For sensing impedance, the sensor 902 may comprise one or more adjustable resistors, such as programmable resistors. For sensing vibration, the sensor 902 may be or comprise one or more components configured to sense a displacement (e.g., vibration) at or near the eye. The sensor 902 may comprise a micro ball sensor, a piezo vibration sensor, a cantilever sensor, a microphone, and the like. The sensor 902 may comprise a piezoelectric, sonic, subsonic, and/or ultrasonic sensor component. The sensor 902 may comprise an emitter/detector pair. The sensor 902 may be configured to generate an electrical signal indicative of the sensed vibration. As such, when characteristics of the ciliary muscle change, the sensor 902 may sense displacement(s) due to such change and may generate the electrical signal indicative of such change or resultant characteristic. For example, there may be various signals detected by the sensor 902 depending on the state that a ciliary muscle is in, such as whether it is contracting or relaxing, or on the type of action that a ciliary muscle is trying to perform, such as causing the eye to focus on a near object or a far object. As a further example, particular states of the ciliary muscle representing one or more characteristics of the ciliary muscle at a given time, may be associated with a particular displacement signature indicative of the particular state. Additionally or alternatively, the change between states of the ciliary muscle may be associated with a particular displacement signature indicative of the particular transition between states. A set of displacement signatures may be determined (e.g., via experimentation) and may be stored for subsequent comparison. The set of displacement signatures may be generated using machine learning, heuristics, signal processing, and/or comparison to one or more predetermined signatures. The set of displacement signatures may be user specific and/or time specific based on actual or predictive use patterns over a period of time.

The sensor 902 may be configured to receive an electrical current flowing through the eye. As such, when the impedance of the eye changes, for example, due to a change in characteristics of the ciliary muscle, the sensor 902 may be configured to the change in characteristics of the ciliary muscle. For example, there may be various signals detected by the sensor 902 depending on the state that a ciliary muscle is in, such as whether it is contracting or relaxing, or on the type of action that a ciliary muscle is trying to perform, such as causing the eye to focus on a near object or a far object.

Figure 11:
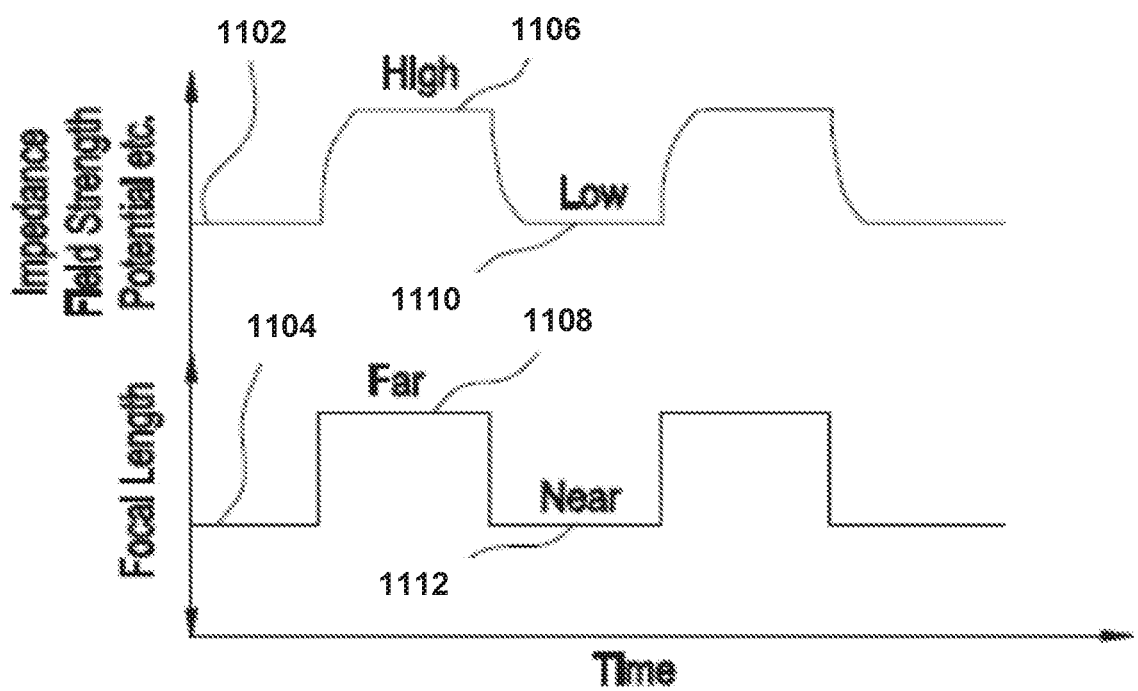
FIG. 11 is a graphical representation demonstrating correlations between measurable electrical parameters and the eye's desired focal length in accordance with the present disclosure.

Example signatures include those associated with the ciliary muscle contracting and relaxing in response to an accommodative stimulus to change lens focus. Peak intensity of muscle movement may occur when the stimulus changes near/far or far/near, which may be represented by a derivative of the signals 1102, 1106 (FIG. 11). This muscle movement causes a corresponding change in tension and movement of the zonules and lens. A characteristic signal associated with such ciliary muscle movement, translated through the zonules and eye to an appropriate sensor, may have distinctly different characteristics in amplitude, duration, and frequency than other signals around the eye. For example, natural accommodation occurs over a period of hundreds of milliseconds and involves both fast changes in reaction to stimulus change and slow changes to maintain focus as part of a feedback loop. Signal processing can differentiate between the fast changes, slow changes, and other signals such as eye movements. As an example, data captured via one or more sensors and/or sensor systems of the present disclosure may be processed based on comparative data such as maximum velocities of saccades and microsaccades of relative to amplitudes, main-sequence diagrams showing peak velocity, duration, and the first peak acceleration as a function of saccadiac magnitude for the saccadic eye movement, and/or main sequence disparity vergence responses, for example. Such processing (e.g., comparison, filtering, etc.) may facilitate the differentiation of noise and may be used to differentiate between the fast changes, slow changes, and other signals such as eye movements. Other comparative data may be collected and used to process the information captured via the sensors and sensor systems of the present disclosure.

Returning to FIG. 9, the sensor circuit 904 or sensor system may be configured to process signals received by the sensor 902. As an example, the sensor circuit 904 may be configured to amplify a signal to facilitate integration of small changes in signal level. As a further example, the sensor circuit 904 may be configured to amplify a signal to a useable level for the remainder of the system, such as giving a signal enough power to be acquired by various components of the sensor circuit 904 and/or the analog-to-digital converter 906. In addition to providing gain, the sensor circuit 904 may include other analog signal conditioning circuitry such as filtering and impedance matching circuitry appropriate to the sensor 902 and sensor circuit 904 output. The sensor circuit 904 may comprise any suitable device for amplifying and conditioning the signal output by the sensor 902. For example, the sensor circuit 904 may simply comprise a single operational amplifier or a more complicated circuit comprising one or more operational amplifiers. As described in further detail in FIG. 11, the sensor circuit 904 may be configured to determine (e.g., measures) a change in the impedance of the eye. As an illustrative example, an error signal may be created by the sensor circuit 904 when an IR drop across the sensor 902 is subtracted from IR drop across the eye. The error signal may be integrated and the resistance value of the sensor 902 may be modified to minimize the error signal. Accordingly, the resistance value of the sensor 902 may be indicative of the impedance across the eye, which may also represent a characteristic of the ciliary muscle. As set forth above, the sensor 902 and the sensor circuit 904 are configured to capture and isolate the signals indicative of characteristic of the ciliary muscle from the noise and other signals produced in or by the eye and convert it to a signal usable ultimately by the system controller 914. The system controller 914 is preferably preprogrammed to recognize the various signals produced by the ciliary muscle under various conditions and provide an appropriate output signal to the actuator 918.

As set forth above, the sensor 902 and the sensor circuit 904 are configured to capture and isolate the signals indicative of characteristic of the ciliary muscle from the noise and other signals produced in or by the eye and convert it to a signal usable ultimately by the system controller 914. The system controller 914 is preferably preprogrammed to recognize the various signals produced by the ciliary muscle under various conditions and provide an appropriate output signal to the actuator 918.

In this exemplary embodiment, the analog-to-digital converter 906 may be used to convert an analog signal output from the amplifier into a digital signal for processing. For example, the analog-to-digital converter 906 may convert an analog signal output from the sensor circuit 904 into a digital signal that may be useable by subsequent or downstream circuits, such as a digital signal processing system 908 or microprocessor. A digital signal processing system or digital signal processor 908 may be utilized for digital signal processing, including one or more of filtering, processing, detecting, and otherwise manipulating/processing sampled data to discern a ciliary muscle signal from noise and interference. The digital signal processor 908 may be pre-programmed with the ciliary muscle responses described above. The digital signal processor 108 may be implemented utilizing analog circuitry, digital circuitry, software and/or preferably a combination thereof. For example, various ciliary muscle signals that may occur within a certain frequency range may be distinguishable from other signals, noise, and interference that occur within other frequency ranges. Certain commonly occurring noise and interference signals may be notched at various stages in the signal acquisition chain utilizing analog or digital filters, for example, harmonics of 50/60 Hz AC mains and fluorescent lights. It may be advantageous to filter various noise and interference signals through a combination of analog and digital signal processing, for example to use differential circuit design techniques to reject common-mode noise that could overload a sensitive amplifier, while performing time- and frequency-domain analysis (e.g. to differentiate ciliary muscle signals from eye movements) in digital signal processing.

A power source 916 supplies power for numerous components comprising the non-contact sensor system. The power may be supplied from a battery, energy harvester, or other suitable means as is known to one of ordinary skill in the art. Essentially, any type of power source may be utilized to provide reliable power for all other components of the system. A ciliary muscle signal, processed from analog to digital, may enable activation of the system controller 914. Furthermore, the system controller 914 may control other aspects of a powered contact lens depending on input from the digital signal processor 908, for example, changing the focus or refractive power of an electronically controlled lens through an actuator 918.

In further alternate exemplary embodiments, the system controller 914 may receive input from sources including one or more of a contact sensor, a blink detector, capacitance sensor, impedance sensor, accelerometer, and/or a fob control. By way of generalization, it may be obvious to one skilled in the art that the method of activating, adjusting parameters (e.g., accommodation threshold, gaze threshold) and/or controlling the system controller 914 may require the use of one or more activation methods. For example, an electronic or powered contact lens may be programmable specific to an individual user, such as programming a lens to recognize both of an individual's ciliary muscle signals when performing various actions, for example, focusing on an object far away, or focusing on an object that is near, and an individual's blink patterns. In some exemplary embodiments, using more than one method to activate an electronic contact lens, such as ciliary muscle signal detection and blink detection, may give the ability for each method to crosscheck with another before modification of a parameter (e.g., or activation/deactivation) of the ophthalmic device occurs. An advantage of crosschecking may include mitigation of false positives, such as minimizing the chance of unintentionally triggering a lens to activate.

In one exemplary embodiment, the crosschecking may involve a voting scheme, wherein a certain number of conditions are met prior to any action taking place. The actuator 918 may comprise any suitable device for implementing a specific action based upon a received command signal. The actuator 918 may comprise an electrical device, a mechanical device, a magnetic device or any combination thereof. The actuator 918 receives a signal from the system controller 914 in addition to power from the power source 916 and produces some action based on the signal from the system controller 914. For example, if the system controller 914 signal is indicative of the wearer trying to focus on a near object, the actuator 918 may be utilized to somehow change the refractive power of the electronic ophthalmic lens.

Figure 10:
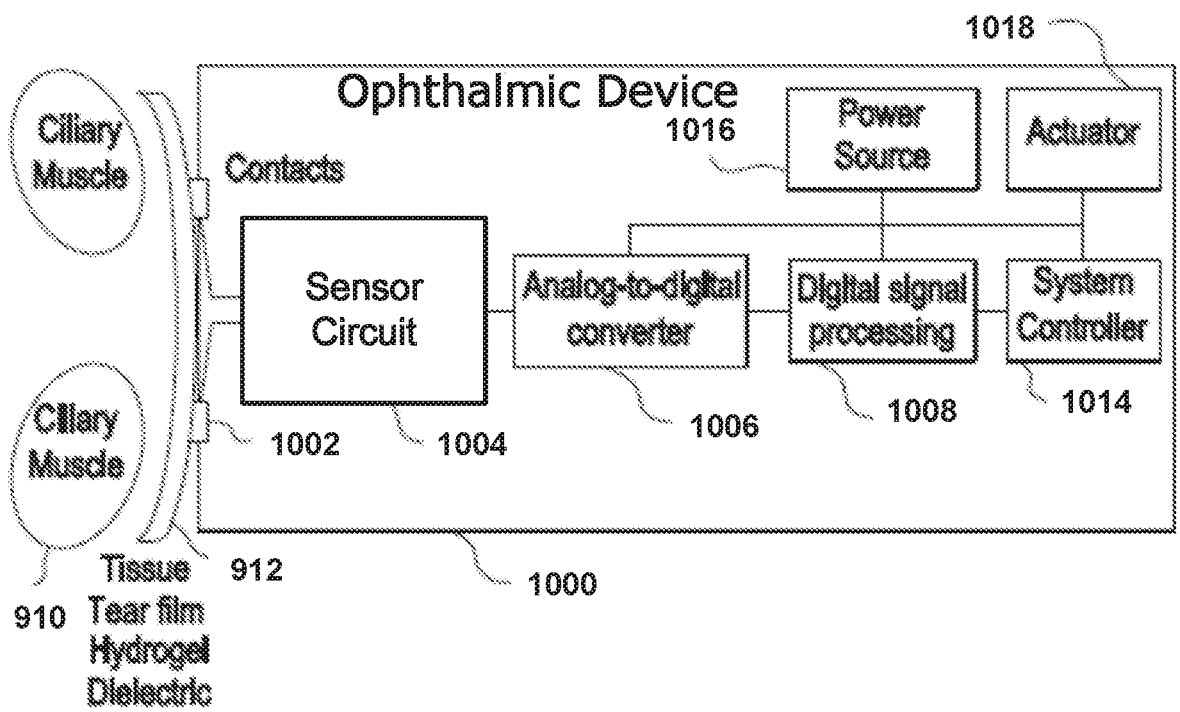
FIG. 10 illustrates an exemplary ophthalmic device comprising a sensor system in accordance with some embodiments of the present disclosure.

FIG. 10 illustrates an ophthalmic device 1000, comprising a sensor system, shown on the front surface of the eye or cornea 912 in accordance with another exemplary embodiment of the present disclosure. In this exemplary embodiment, a sensor system may comprise a contact or multiple contacts 1002, a sensor circuit 1004, an analog-to-digital converter 1006, a digital signal processor 1008, a power source 1016, an actuator 1018, and a system controller 1014. The ciliary muscle 910 is located behind the front eye surface or cornea 912. The ophthalmic device 1000 is placed onto the front surface of the eye 912, such that the electronic circuitry of the sensor may be utilized to implement the neuromuscular sensing of the present disclosure. The components of this exemplary system are similar to and perform the same functions as those illustrated in FIG. 9, with the exception of contacts 1002 and the sensor circuit 1004. In other words, since direct contacts 1002 are utilized, there is no need for an antenna or an amplifier to amplify and condition the signal received by the antenna.

In the illustrated exemplary embodiment, the contacts 1002 may provide for a direct electrical connection to the tear film and the eye surface. For example, the contacts 1002 may be implemented as metal contacts that are exposed on the back curve of the ophthalmic device 1000 and be made of biocompatible conductive materials, such as gold or titanium. Furthermore, the contact lens polymer may be molded around the contacts 1002, which may aid in comfort on the eye and provide improved conductivity through the ophthalmic device 1000. Additionally, the contacts 1002 may provide for a low resistance connection between the eye's surface 912 and the electronic circuitry within the ophthalmic device 1000. Four-terminal sensing, also known as Kelvin sensing, may be utilized to mitigate contact resistance effects on the eye. The sensor circuit 1004 may emit a signal with several constituent frequencies or a frequency sweep, while measuring the voltage/current across the contacts 1002.

In an alternate exemplary embodiment, the sensor circuit 1004 may be configured to sense a vibration, a change in impedance, and/or the like produced by the contraction or relaxation of the ciliary muscle 910. It is important to note that various types of sensors may be utilized, given that the eye comprises various fluids, including tears which are excellent conductors. The sensor circuit 1004 may be configured to measure vibration, wherein the vibration may change based upon what a ciliary muscle is trying to do, such as contracting or relaxing. In this exemplary embodiment, the analog-to-digital converter 1006 and the digital signal processing 1008 may be configured differently for a contact-based sensor as opposed to a non-contact based sensor, as described in FIG. 9. For example, there may be a different sample rate, a different resolution, and different signal processing algorithm 1008.

In an alternate exemplary embodiment, the sensor circuit 1004 may be configured to read a potential difference across the eye arising from a voltage or current produced by the contraction or relaxation of the ciliary muscle 910. It is important to note that various types of sensors may be utilized, given that the eye comprises various fluids, including tears which are excellent conductors. The sensor circuit 1004 may be configured to measure the impedance of an eye wherein the impedance may change in a certain location based upon what a ciliary muscle is trying to do, such as contracting or relaxing. In this exemplary embodiment, the analog-to-digital converter 1006 and the digital signal processing 1008 may be configured differently for a contact-based sensor as opposed to a non-contact based sensor, as described in FIG. 9. For example, there may be a different sample rate, a different resolution, and different signal processing algorithm 208.

FIG. 11 illustrates a graph demonstrating correlations between measurable electrical parameters and the eye's focal length as described in the referenced literature. Trace 1102 is a representation of an electrically measurable signal in or on the eye. For example, such signals may be detected as one or more of impedance, voltage potential, induced electromagnetic field, and other measurable parameters (e.g., displacement). Trace 1104 is a representation of a desired focal length wherein for example, if clinical subjects focused on objects at 0.2 and 2.0 meter distances, the ciliary muscle may undergo a corresponding change in measurable electrical parameters and displacement characteristics accordingly, depending on the distance of focus. However, using the same example, the actual focal length of a lens may not change or only changes minimally, such as in cases where a person may be presbyopic and the lens of the eye is too rigid and unable to accommodate for a change in focus, even where the ciliary muscles are responding to the change.

As described in the literature, there is a correlation between a measurable electrical signal and a focal length. As illustrated in FIG. 11, impedance is high 106 when the focal length is far 1108 and impedance is low 1110 when the focal length is near 1112. Additionally, as described in the literature but not illustrated in FIG. 11, a correlation exists between the amplitude of traces 1102 and 1104 for intermediate values. Moreover, displacement signatures may be associated (e.g., correlated) with a particular state of the ciliary muscle and/or transitions between such states, which may also be associated with an impedance and/or change in such impedance.

In some exemplary embodiments, characteristics of an electrical signal (e.g., trace 1102, 1104) such as shape, frequency content, timing, and amplitude, may vary due to several factors including one or more of a detection method utilized (e.g., vibration, impedance, or field strength), an individual's eye physiology, ciliary muscle fatigue, electrolyte levels in the eye, state of presbyopia, interference, and focal length. For example, depending on the type of detection method used, the correlation between desired focus and measurable electrical parameter may have the opposite polarity from what is illustrated in FIG. 11. The characteristics of the electrical signal may be used to determine a dwell characteristic, user activity, context, and/or whether to update a parameter (e.g., accommodation threshold, gaze threshold).

Additionally, for example, a signal may be distorted from carrying one or more of significant noise, interference from other muscles, and interference from various environmental sources or due to the effects of aging, disease or genetics. Accordingly, studies of eye response and individual user measurement and training may be used to program the digital signal circuitry to properly detect the eye's desired focal length. Parameters of the digital signal processing may be adjusted in response to other measurements, for example, time of day, measured electrolyte levels, ambient light levels and the like. Furthermore, recorded samples of a user's eye focus signals may be used in conjunction with interference detection and mitigation techniques. It is important to note that any type of sensor may be utilized in accordance with the present disclosure. As long as there is muscle movement associated with changing conditions, it may be sensed, processed and utilized to enhance, augment or simply provide vision correction.

Figure 12:
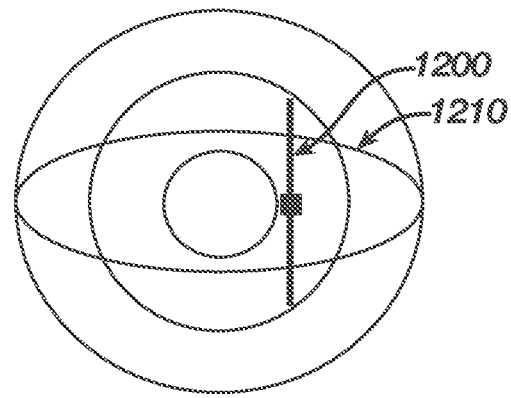
FIG. 12 is a diagrammatic representation of an exemplary electronic system incorporated into a contact lens for detecting eyelid position in accordance with the present disclosure.
Figure 13:
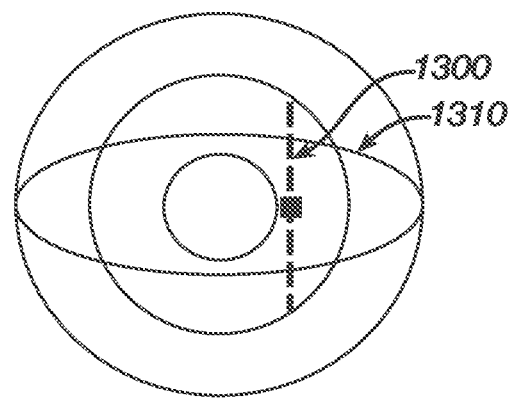
FIG. 13 is a diagrammatic representation of an exemplary electronic system incorporated into a contact lens for detecting eyelid position in accordance with the present disclosure.
Figure 14:
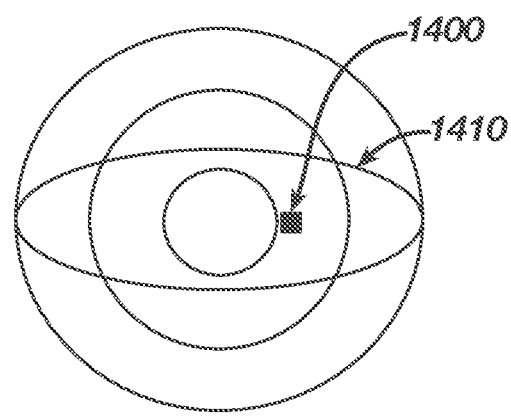
FIG. 14 is a diagrammatic representation of an exemplary electronic system incorporated into a contact lens for detecting eyelid position in accordance with the present disclosure.
Figure 15A:
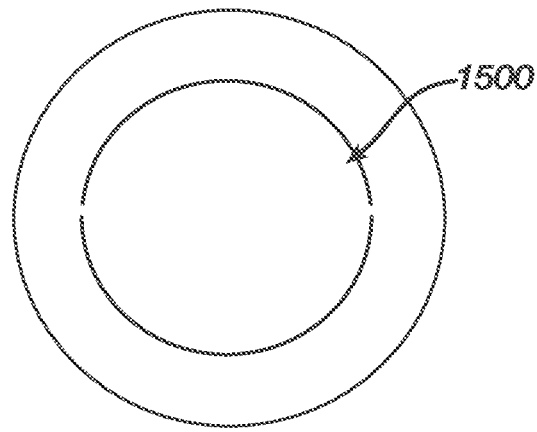
FIG. 15A is a diagrammatic representation of an exemplary electronic system incorporated into a contact lens for detecting eyelid position in accordance with the present disclosure.
Figure 15B:
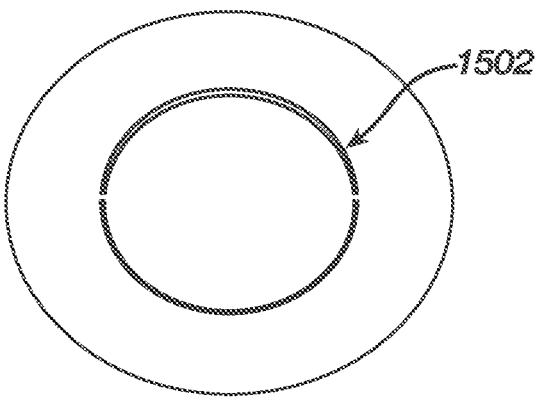
FIG. 15B is a diagrammatic representation of an exemplary electronic system incorporated into a contact lens for detecting eyelid position in accordance with the present disclosure.
Figure 15C:
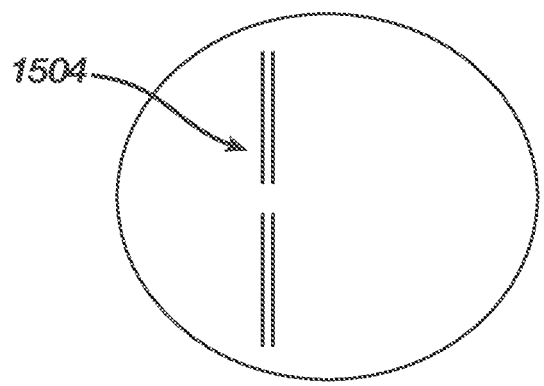
FIG. 15C is a diagrammatic representation of an exemplary electronic system incorporated into a contact lens for detecting eyelid position in accordance with the present disclosure.
Figure 16A:
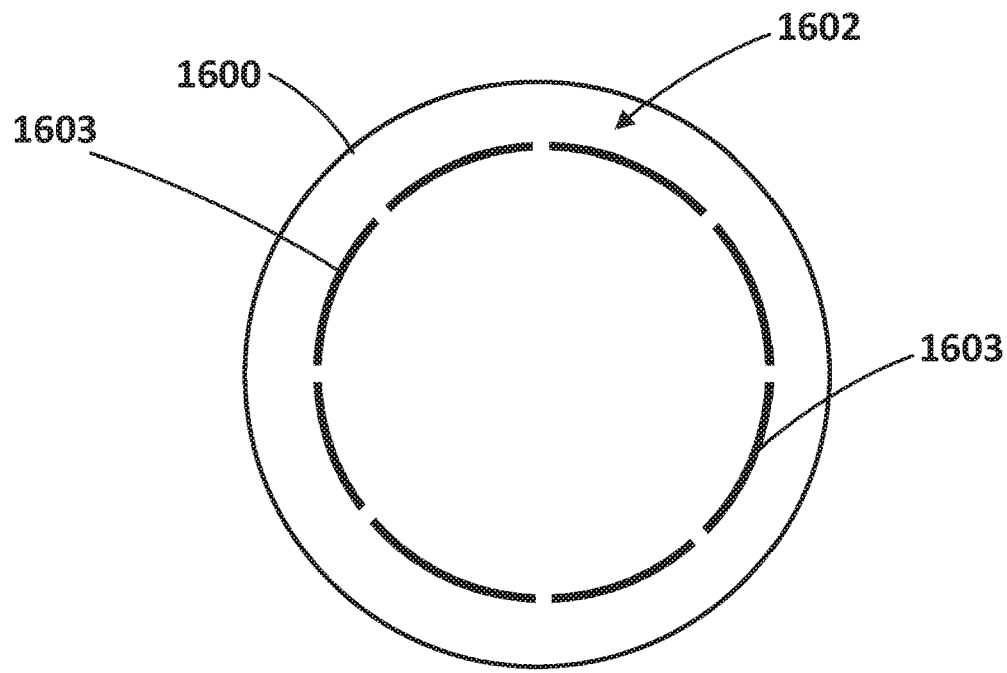
FIG. 16A is a diagrammatic representation of an exemplary electronic system incorporated into a contact lens for detecting eyelid position in accordance with the present disclosure.
Figure 16B:
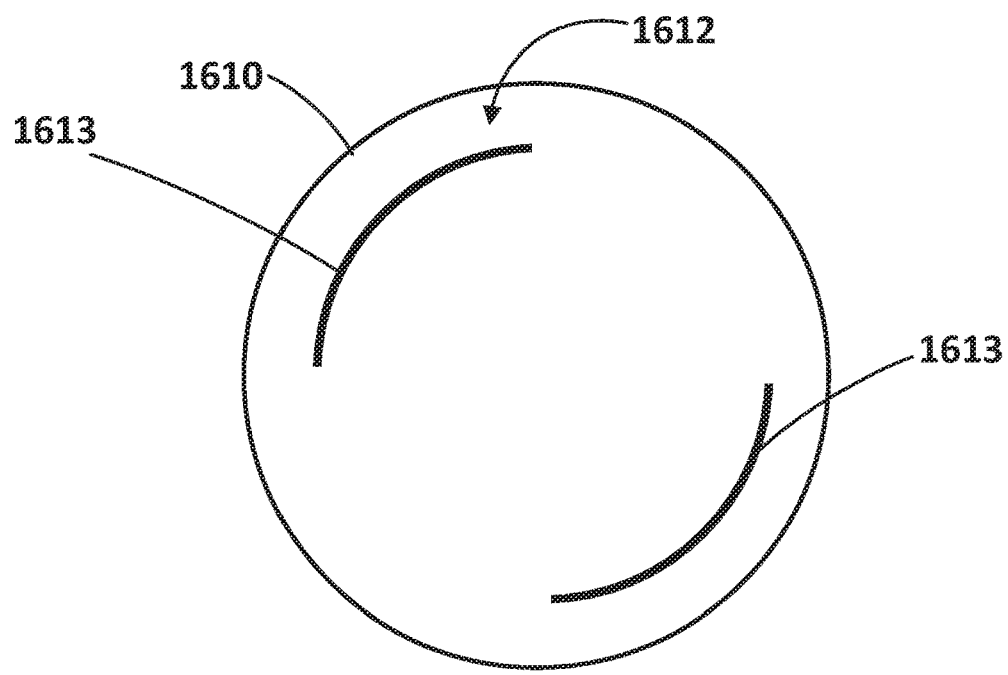
FIG. 16B is a diagrammatic representation of an exemplary electronic system incorporated into a contact lens for detecting eyelid position in accordance with the present disclosure.

In an aspect, dwell characteristics associated with movement of an eyelid or an eye may be determined based on one or more capacitive touch sensors. The capacitive touch sensors may be used to track movements of the eye of the use. The movements may be recognized as a dwell characteristic, a gesture, a user activity (e.g., for determining context), and/or the like. The movements may be used as trigger for causing output of a signal indicative of an action perform. The movements may be used as a trigger for adjusting a parameter, such as a dwell mode, dwell threshold, and/or the like. The capacitive touch sensors may be used to sense a capacitance upon an eye of the user of the ophthalmic device. As an example, the capacitive touch sensors may be configured to detect a capacitance that may be affected by a position of one or more of an upper eyelid and a lower eyelid of the user. As such, the sensed capacitance may be indicative of a position of the eyelid(s) and may represent a gaze or position of the eye. One or more of the capacitive touch sensors may be configured as linear sensor 1200 (FIG. 12), a segmented sensor 1300 (FIG. 13), and/or an integrating sensor 1400 (FIG. 14) configured to integrate a response over a sensor area. In the various configurations illustrated in FIGS. 12-14, the sensors 1200, 1300, 1400 may be configured to sense a capacitance due at least in part to a position of an eyelid 1210, 1310, 1410. Additionally, or alternatively, the sensors may be configured as a dual wire single capacitive sensor 1500 (FIG. 15A)

and/or a dual wire dual capacitive sensor 1502 (FIG. 15B) having a generally curvilinear configuration. Additionally, or alternatively, the sensors may be configured as a dual wire dual capacitive sensor 1504 (FIG. 15C) having a generally straight configuration. Additionally, or alternatively, the sensors may be configured in a generally annular configuration. Any number of sensors may be configured. For example, FIG. 16A illustrates an ophthalmic device 1600 comprising a sensor 1602 having eight traces or electrodes 1603 configured in a generally annular configuration. As a further example, FIG. 16B illustrates an ophthalmic device 1610 comprising a sensor 1612 having two traces or electrodes 1613 configured in a generally annular configuration, wherein each of the electrodes 1613 have a generally curvilinear shape and extend less than half of the circumference of the ophthalmic device 1610.

Figure 17A:
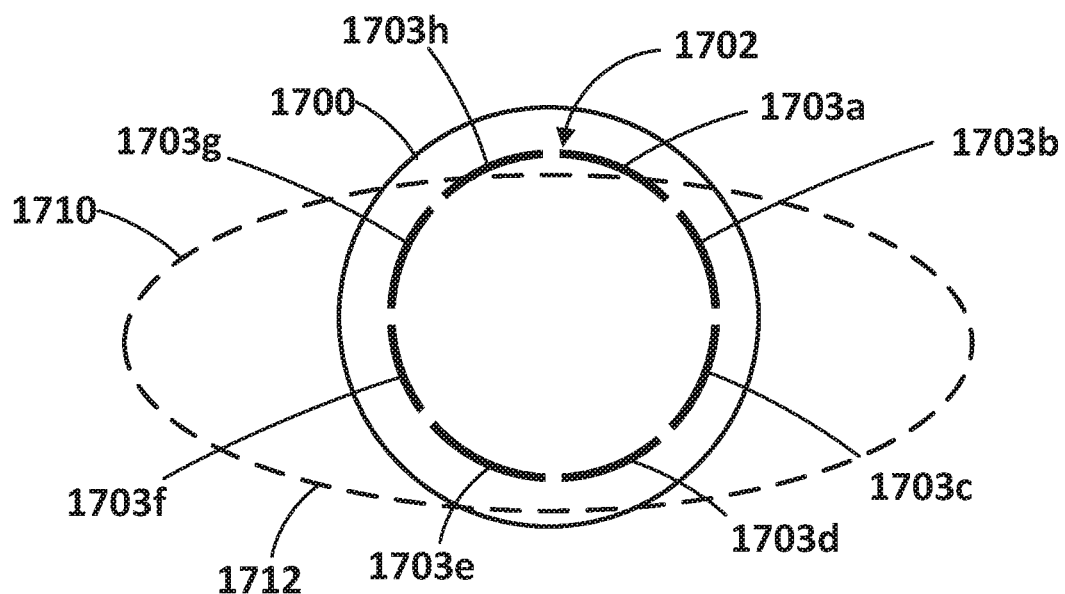
FIG. 17A is a diagrammatic representation of an exemplary electronic system incorporated into a contact lens for detecting eyelid position in accordance with the present disclosure.
Figure 17B:
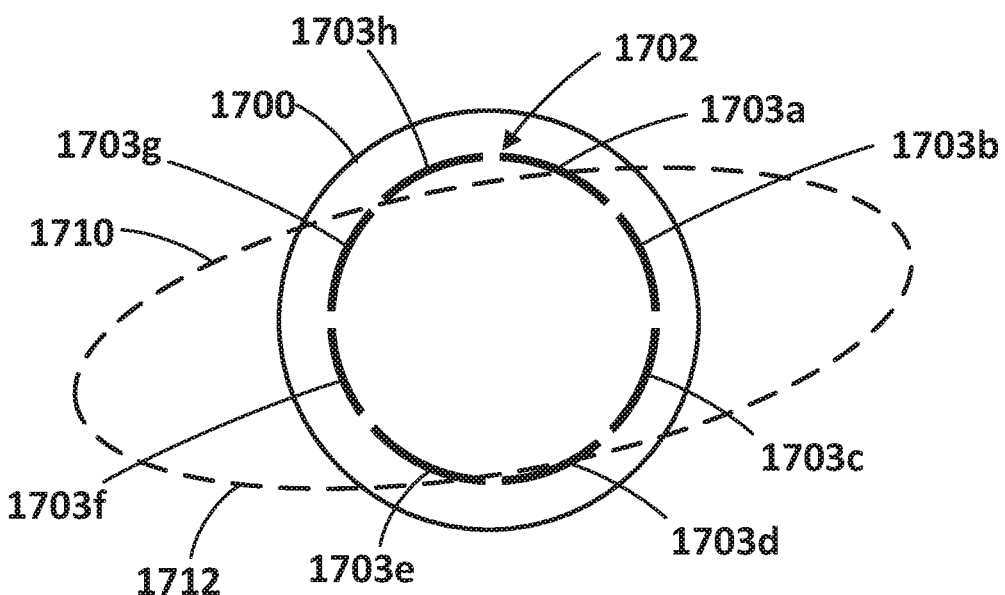
FIG. 17B is a diagrammatic representation of an exemplary electronic system incorporated into a contact lens for detecting eyelid position in accordance with the present disclosure.

FIGS. 17A, 17B, and 17C illustrate various positions of the eyelids 1710, 1712 as they may overlay the electrodes 1703 of a sensor 1702. As the gaze of a user changes, the position of the eyelids 1710, 1712 changes and may overlay different portions of the sensor 1702, thereby causing fluctuation in capacitance measurement taken from one or more of the electrodes 1703.

As shown in FIG. 17A, a gaze angle may be taken as a zero degree down gaze, where the upper eyelid 1720 overlays electrode 1703a and electrode 1703h and the lower eyelid 1712 overlays none of the electrodes 1703a-h. As such, the capacitance measurement at each of the electrodes 1703a-h may provide a capacitive sensing signature representative of the zero degree down gaze. In particular, electrode 1703a and electrode 1703h may detect a capacitance measurement indicative of the overlaying upper eyelid 1720. This information may be stored, for example, via a system controller 101 (FIG. 1) and may be referenced subsequently. As an example, when a subsequent capacitance measurement is found to be the same or similar to the stored measurement, the positions of the eyelids 1720, 1712 may be determined. Additionally, or alternatively, the eye gaze may be determined. As a further example, the stored measurements may represent the activation or deactivation of a particular electrode 1703 have a sensed capacitance over a preset threshold. For example, the stored measurements may indicate the for a zero degree down gaze, the electrodes 1703a, 1703h will be activated, but the other electrodes 1703b-1703g will be deactivated. Capacitance measurements may be absolute, binary, actual, and/or conditioned in various manners.

As shown in FIG. 17B, a gaze angle may be taken as a twenty-five degree down gaze, where the upper eyelid 1720 overlays electrode 1703a and electrode 1703h and the lower eyelid 1712 overlays electrode 1703d and electrode 1703e. As such, the capacitance measurement at each of the electrodes 1703a-h may provide a capacitive sensing signature representative of the twenty-five degree down gaze. In particular, electrode 1703a and electrode 1703h may detect a capacitance measurement indicative of the overlaying upper eyelid 1720. Electrode 1703d and electrode 1703e may detect a capacitance measurement indicative of the overlaying lower eyelid 1712. This information may be stored, for example, via a system controller 101 (FIG. 1) and may be referenced subsequently. As an example, when a subsequent capacitance measurement is found to be the same or similar to the stored measurement, the positions of the eyelids 1720, 1712 may be determined. Additionally, or alternatively, the eye gaze may be determined. The eye gaze (e.g., or eye gaze angle) and/or the position of an eyelid may be used to determine whether a movement is intentional and/or relates to a gesture (e.g., to control an ophthalmic device). As a further example, the stored measurements may represent the activation or deactivation of a particular electrode 1703 have a sensed capacitance over a preset threshold. For example, the stored measurements may indicate the for a zero degree down gaze, the electrodes 1703a, 1703d, 1703e, 1703h will be activated, but the other electrodes will be deactivated. Capacitance measurements may be absolute, binary, actual, and/or conditioned in various manners.

As shown in FIG. 17C, a gaze angle may be taken as a forty-five degree down gaze, where the upper eyelid 1720 overlays electrode 1703a and electrode 1703h and the lower eyelid 1712 overlays electrode 1703c and electrode 1703f. As such, the capacitance measurement at each of the electrodes 1703a-h may provide a capacitive sensing signature representative of the forty-five degree down gaze. In particular, electrode 1703a and electrode 1703h may detect a capacitance measurement indicative of the overlaying upper eyelid 1720. Electrode 1703c and electrode 1703f may detect a capacitance measurement indicative of the overlaying lower eyelid 1712. This information may be stored, for example, via a system controller 101 (FIG. 1) and may be referenced subsequently. As an example, when a subsequent capacitance measurement is found to be the same or similar to the stored measurement, the positions of the eyelids 1720, 1712 may be determined. Additionally, or alternatively, the eye gaze may be determined. The capacitance measurement, the position of an eyelid, eye angle, and/or the eye gaze may be used to determine whether a movement is intentional and/or relates to a gesture (e.g., for controlling an ophthalmic device). For example, the capacitance measurement, the position of an eyelid, eye angle, and/or the eye gaze may be analyzed with timing information (e.g., length of time a position is held), historical information (e.g., previous and/or subsequent movements) to determine whether a movement is intentional and/or relates to a gesture (e.g., for controlling an ophthalmic device). As a further example, the stored measurements may represent the activation or deactivation of a particular electrode 1703 have a sensed capacitance over a preset threshold. For example, the stored measurements may indicate the for a zero degree down gaze, the electrodes 1703a, 1703c, 1703f, 1703h will be activated, but the other electrodes will be deactivated. Capacitance measurements may be absolute, binary, actual, and/or conditioned in various manners. The capacitance measurements may be used to determine a dwell characteristic, user activity, context, and/or whether to update a parameter (e.g., accommodation threshold, gaze threshold).

The capacitive touch sensors may comprise a variable capacitor, which may be implemented in a physical manner such that the capacitance varies with proximity or touch, for example, by implementing a grid covered by a dielectric. Sensor conditioners create an output signal proportional to the capacitance, for example, by measuring the change in an oscillator comprising the variable capacitor or by sensing the ratio of the variable capacitor to a fixed capacitor with a fixed-frequency AC signal. The output of the sensor conditioners may be combined with a multiplexer to reduce downstream circuitry.

Figure 18:
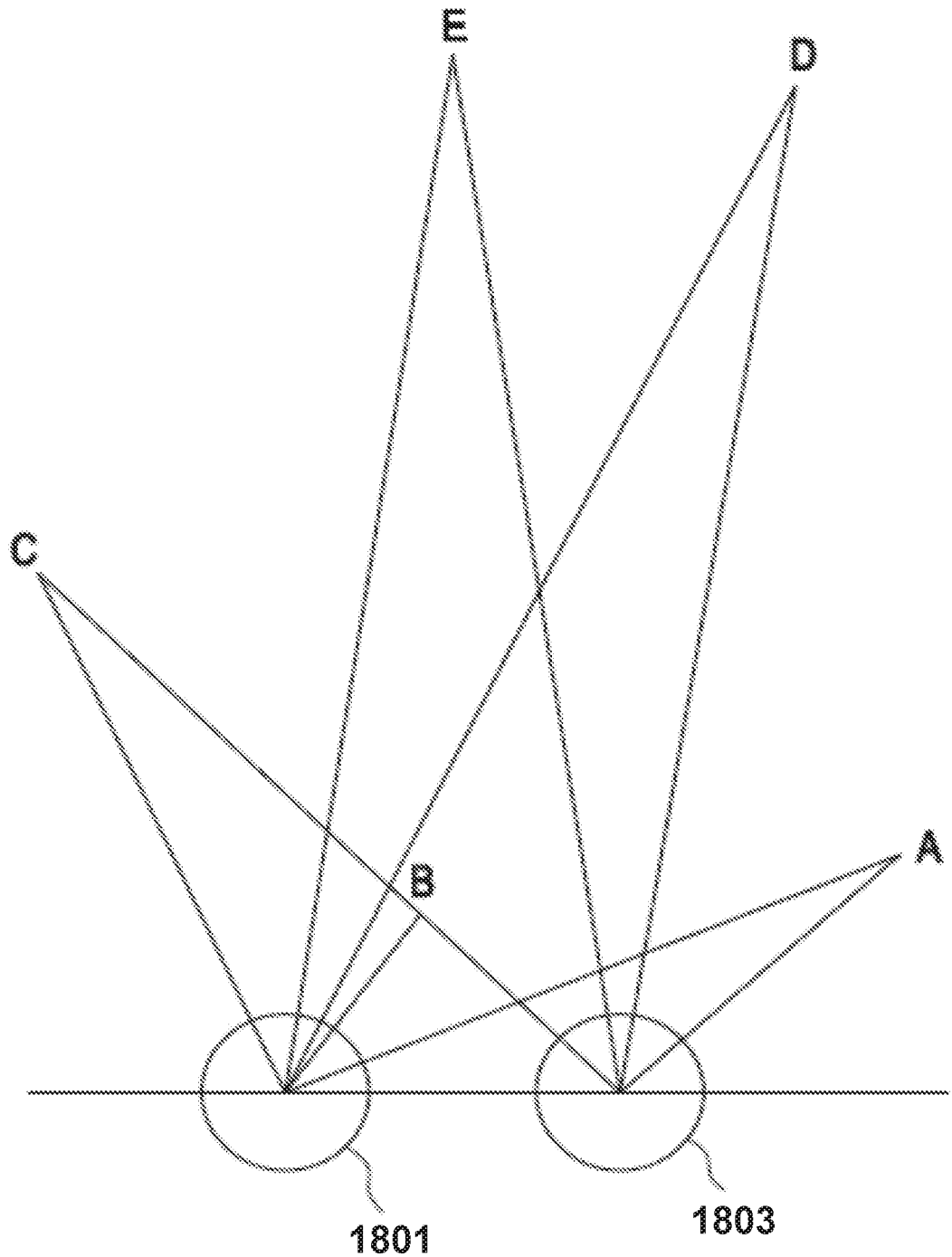
FIG. 18 is a diagrammatic representation of the geometry associated with various gaze directions in two dimensions in accordance with the present disclosure.

FIG. 18 illustrates the geometric systems associated with various gaze directions. FIG. 18 is a top view. Eyes 1801 and 1803 are shown gazing upon various targets labeled A, B, C, D, and E. A line connects each eye 1801 and 1803 to each 15 target. A triangle is formed by each of the two lines connecting the eyes 1801 and 1803 with a given target in addition to a line connecting both eyes 1801 and 1803. As may be seen in the illustration, the angles between the direction of gaze in each eye 1801 and 1803 and the line between the two eyes 1801 and 1803 varies for each target. These angles may be measured by the sensor system, determined from indirect sensor measurements, or may only be shown for illustrative purposes. Although shown in two dimensional space for simplicity of illustration, it should be apparent that gaze occurs in three-dimensional space with the corresponding addition of an additional axis. Targets A and B are shown relatively near to the eyes 1801 and 1803, for example, to be read with near-focus accommodation. Target A is to the right of both eyes 1801 and 1803, hence both eyes 1801 and 1803 are pointing right. Measuring the angle formed anticlockwise between the horizontal axis, illustrated collinear with the line connecting the two eyes 1801 and 1803, and direction of gaze, both angles are acute for target A. Now referring to target B the eyes 1801 and 1803 are converged on a target in front of and between both eyes 1801 and 1803. Hence the angle, previously defined as anticlockwise from the horizontal axis and the direction of gaze, is obtuse for the right eye 1803 and acute for the left eye 1801. A suitable sensor system will differentiate the positional difference between targets A and B with suitable accuracy for the application of concern. Target C is shown at intermediate distance for the special case of the right eye 1803 having the same direction of gaze and angle as target B. The gaze direction varies between targets B and C allowing a gaze direction determination system using inputs from both eyes 1801 and 1803 to determine the direction of gaze. Further, a case could be illustrated where another target F lies above target B in three-dimensional space.

In FIG. 18, the angles from the horizontal axis would be identical to those illustrated for target B. However, the angles normal to the page extending in three-dimensional space would not be equal between the targets. Finally, targets D and E are shown as distant objects. These examples illustrate that as the object under gaze is farther away, the angular difference at the eyes 1801 and 1403 between distant points becomes smaller. A suitable system for detecting gaze direction would have sufficient accuracy to 15 differentiate between small, distant objects.

The present methods and systems may determine one or more angles of movement associated with the gaze of the user (e.g., regardless of whether the user's eyelids are open or closed). The angle of movement may be used to determine a dwell characteristic, an activity of a user (e.g., reading, watching media, driving, talking to others), whether to filter out a movement of the eye, whether to adjust a threshold (e.g., accommodation threshold, gaze threshold), whether to adjust a hysteresis value, and/or the like.

It is important to note that the above described elements may be realized in hardware, in software or in a combination of hardware and software. In addition, the communication channel may comprise any include various forms of wireless communications. The wireless communication channel may be configured for high frequency electromagnetic signals, low frequency electromagnetic signals, visible light signals, infrared light signals, and ultrasonic modulated signals. The wireless channel may further be used to supply power to the internal embedded power source acting as rechargeable power means.

The present disclosure may be a system, a method, and/or a computer program product. The computer program product being used by a controller for causing the controller to carry out aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. An ophthalmic system comprising:
    a first ophthalmic device configured to be disposed within or upon an eye of a user; and
    a first sensor system disposed in or on the first ophthalmic device, the first sensor system comprising a first sensor and a first processor operably connected to the first sensor and configured for:
        causing storage of a history of movement of the eye;
        determining, based on the history of movement, a dwell characteristic indicating a distance at which the eye is fixated when an event occurs; and
        causing output of a signal indicative of performing an action in response to determining the dwell characteristic.

2. The ophthalmic system of claim 1, wherein causing storage of a history of movement of the eye comprises storing data from one or more of a capacitive sensor configured to detect eye position or eye lid position, an impedance sensor configured to detect eye muscle movements, a vergence sensor configured to detect eye vergence, an accelerometer configured to detect eye movement, or a vibration sensor configured to detect eye movements.

3. The ophthalmic system of claim 1, wherein the event comprises activating the first ophthalmic device.

4. The ophthalmic system of claim 1, wherein the event comprises the eye remaining fixated at the distance for a minimum amount of time.

5. The ophthalmic system of claim 1, wherein the causing output of the signal indicative of performing the action comprises causing adjustment of an accommodation threshold for activating a lens to perform accommodation operation.

6. The ophthalmic system of claim 5, wherein the accommodation threshold comprises a distance threshold indicative of a minimum distance at which the eye is fixated before activating the lens to perform the accommodation operation, and wherein the accommodation threshold comprises a time threshold indicative of a minimum time at which the eye is fixated at a distance before activating the lens to perform the accommodation operation.

7. The ophthalmic system of claim 5, wherein the accommodation operation comprises adjusting the lens to allow the eye to focus at a distance.

8. The ophthalmic system of claim 1, wherein the first processor being configured for causing output of a signal indicative of performing an action comprises the first processor being configured for adjusting a parameter of the first sensor system.

9. The ophthalmic system of claim 8, wherein the parameter comprises a threshold for switching between an accommodation mode and a gaze mode, wherein the accommodation mode is configured for focusing at distances nearer the user and the gaze mode is configured for focusing at distances farther from the user.

10. The ophthalmic system of claim 9, wherein the parameter comprises a hysteresis value indicative of a difference between an accommodation threshold for enabling the accommodation mode and a gaze threshold for enabling the gaze mode.

11. The ophthalmic system of claim 8, wherein adjusting the parameter comprises increasing a value of the parameter.

12. The ophthalmic system of claim 8, wherein the first processor is further configured for receiving input from the user associated with adjusting the parameter, wherein the input indicates whether the user accepts or rejects the adjusting of the parameter.

13. The ophthalmic system of claim 12, wherein the first processor is further configured to adjust the dwell characteristic if the input indicates that the user rejects the adjusting of the parameter.

14. The ophthalmic system of claim 1, wherein causing storage of the history of movement of the eye comprises causing storage in a local storage of the first sensor system.

15. The ophthalmic system of claim 1, wherein causing storage of the history of movement of the eye comprises causing storage in remote storage external to first sensor system.

16. The ophthalmic system of claim 1, wherein the first ophthalmic device comprises a contact lens or an implantable lens, or a combination of both.

17. The ophthalmic system of claim 1, wherein the first processor is further configured to determine an accommodation threshold based an instruction from the user indicating the accommodation threshold.

18. The ophthalmic system of claim 17, wherein the accommodation threshold comprises a user defined accommodation threshold, wherein adjusting the accommodation threshold comprises adjusting the user defined threshold.

19. The ophthalmic system of claim 1, wherein the first processor is further configured for determining that a current movement of the eye satisfies the dwell characteristic, and wherein causing output of the signal indicative of performing the action is performed in response to determining that the eye satisfies the dwell characteristic.

20. An ophthalmic system comprising:
a first ophthalmic device configured to be disposed within or upon an eye of a user; and
a first sensor system disposed in or on the first ophthalmic device, the first sensor system comprising a first sensor and a first processor operably connected to the first sensor and configured for:
causing storage of a history of movement of at least one of the eye or an eye lid of the eye;
determining, based on the history of movement, a characteristic of the user;
determining that a current movement of at least one of the eye or the eye lid matches the characteristic of the user; and
filtering sensor data from the first sensor associated with the current movement in response to determining that the current movement of at least one of the eye or the eye lid matches the characteristic of the user.

21. The ophthalmic system of claim 20, wherein the characteristic of the user comprises a blink rate.

22. The ophthalmic system of claim 21, wherein filtering the sensor data from the first sensor associated with the current movement comprises filtering involuntary blink movements based on the blink rate.

23. The ophthalmic system of claim 20, wherein the characteristic of the user comprises a microsaccades movement.

24. The ophthalmic system of claim 23, wherein filtering the sensor data from the first sensor associated with the current movement comprises filtering microsaccades movement.

25. The ophthalmic system of claim 20, wherein the characteristic of the user comprises a dwell time indicative of a minimum time that the eye is fixated at a distance before activating a lens to perform an accommodation operation, wherein filtering the sensor data from the first sensor associated with the current movement comprises filtering sensor data associated with movement of the eye that does not satisfy the dwell time.

26. The ophthalmic system of claim 20, wherein filtering sensor data from the first sensor associated with the current movement comprises rejecting the sensor data.

27. The ophthalmic system of claim 20, wherein filtering sensor data from the first sensor associated with the current movement comprises determining that the sensor data is not indicative of a command from the user.

28. The ophthalmic system of claim 20, wherein causing storage of the history of movement of the eye comprises causing storage in a local storage of the first sensor system.

29. The ophthalmic system of claim 20, wherein causing storage of the history of movement of the eye comprises causing storage in remote storage external to first sensor system.

30. The ophthalmic system of claim 20, wherein the first ophthalmic device comprises a contact lens or an implantable lens, or a combination of both.

31. A method comprising:
receiving, by a first sensor system disposed on or in a first ophthalmic device, sensor data representing movement of an eye of a user, wherein the first ophthalmic device is disposed within or upon an eye of the user;
causing, based on the sensor data, storage of a history of movement of the eye;
determining, based on the history of movement, a dwell characteristic indicating a distance at which the eye is fixated when an event occurs; and
causing output of a signal indicative of performing an action in response to determining the dwell characteristic.

32. The method of claim 31, wherein causing storage of a history of movement of the eye comprises storing data from one or more of a capacitive sensor configured to detect eye position or eye lid position, an impedance sensor configured to detect eye muscle movements, a vergence sensor configured to detect eye vergence, an accelerometer configured to detect eye movement, or a vibration sensor configured to detect eye movements.

33. The method of claim 31, wherein the event comprises activating the first ophthalmic device.

34. The method of claim 31, wherein the event comprises the eye remaining fixated at the distance for a minimum amount of time.

35. The method of claim 31, wherein causing output of the signal indicative of performing the action comprises causing adjustment of an accommodation threshold for activating a lens to perform an accommodation operation.

36. The method of claim 35, wherein the accommodation threshold comprises a distance threshold indicative of a minimum distance at which the eye is fixated before activating the lens to perform the accommodation operation, and wherein the accommodation threshold comprises a time threshold indicative of a minimum time at which the eye is fixated at a distance before activating the lens to perform the accommodation operation.

37. The method of claim 35, wherein the accommodation operation comprises adjusting the lens to allow the eye to focus at a distance.

38. The method of claim 31, wherein causing output of a signal indicative of performing an action comprises increasing an accommodation threshold.

39. The method of claim 31, wherein causing output of a signal indicative of performing an action comprises causing adjustment of a parameter of the first sensor system.

40. The method of claim 39, wherein the parameter comprises a threshold for switching between an accommodation mode and a gaze mode, wherein the accommodation mode is configured for focusing at distances nearer the user and the gaze mode is configured for focusing at distances farther from the user.

41. The method of claim 40, wherein the parameter comprises a hysteresis value indicative of a difference between an accommodation threshold for enabling the accommodation mode and a gaze threshold for enabling the gaze mode.

42. The method of claim 39, further comprising receiving input from the user associated with adjusting the parameter, wherein the input indicates whether the user accepts or rejects the adjusting of the parameter.

43. The method of claim 42, further comprising adjusting the dwell characteristic if the input indicates that the user rejects the adjusting of the parameter.

44. The method of claim 31, wherein causing storage of the history of movement of the eye comprises causing storage in a local storage of the first sensor system.

45. The method of claim 31, wherein causing storage of the history of movement of the eye comprises causing storage in remote storage external to first sensor system.

46. The method of claim 31, wherein the first ophthalmic device comprises a contact lens or an implantable lens, or a combination of both.

47. The method of claim 31, further comprising determining an accommodation threshold based an instruction from the user indicating the accommodation threshold.

48. The method of claim 47, wherein the accommodation threshold comprises a user defined accommodation threshold, wherein causing output of the signal indicative of performing the action comprises adjusting the user defined threshold.

49. The method of claim 31, further comprising determining that a current movement of the eye satisfies the dwell characteristic, and wherein causing output of the signal indicative of performing the action is performed in response to determining that the eye satisfies the dwell characteristic.

50. A method comprising:
receiving, by a first sensor system comprising a first sensor disposed on or in a first ophthalmic device, sensor data representing movement of an eye of a user, wherein the first ophthalmic device is disposed within or upon an eye of the user;
causing, based on the sensor data, storage of a history of movement of at least one of the eye or an eye lid of the eye;
determining, based on the history of movement, a characteristic of the user;
determining that a current movement of at least one of the eye or the eye lid matches the characteristic of the user; and
filtering sensor data from the first sensor associated with the current movement in response to determining that the current movement of at least one of the eye or the eye lid matches the characteristic of the user.

51. The method of claim 50, wherein the characteristic of the user comprises a blink rate.

52. The method of claim 51, wherein filtering the sensor data from the first sensor associated with the current movement comprises filtering involuntary blink movements based on the blink rate.

53. The method of claim 50, wherein the characteristic of the user comprises a microsaccades movement.

54. The method of claim 53, wherein filtering the sensor data from the first sensor associated with the current movement comprises filtering microsaccades movement.

55. The method of claim 50, wherein the characteristic of the user comprises a dwell time indicative of a minimum time that the eye is fixated at a distance before activating a lens to perform an accommodation operation, wherein filtering the sensor data from the first sensor associated with the current movement comprises filtering sensor data associated with movement of the eye that does not satisfy the dwell time.

56. The method of claim 50, wherein filtering sensor data from the first sensor associated with the current movement comprises rejecting the sensor data.

57. The method of claim 50, wherein filtering sensor data from the first sensor associated with the current movement comprises determining that the sensor data is not indicative of a command from the user.

58. The method of claim 50, wherein causing storage of the history of movement of the eye comprises causing storage in a local storage of the first sensor system.

59. The method of claim 50, wherein causing storage of the history of movement of the eye comprises causing storage in remote storage external to first sensor system.

60. The method of claim 50, wherein the first ophthalmic device comprises a contact lens or an implantable lens, or a combination of both.

* * * * *